US008518896B2

(12) United States Patent
Magnani et al.

(10) Patent No.: US 8,518,896 B2
(45) Date of Patent: Aug. 27, 2013

(54) TREATMENT OF CANCERS OF THE BLOOD USING SELECTED GLYCOMIMETIC COMPOUNDS

(75) Inventors: John L. Magnani, Gaithersburg, MD (US); John T. Patton, Jr., Gaithersburg, MD (US); Theodore A. G. Smith, Ijamsville, MD (US)

(73) Assignee: Glycomimetics, Inc., Gaithersburg, MD (US)

( * ) Notice: Subject to any disclaimer, the term of this patent is extended or adjusted under 35 U.S.C. 154(b) by 524 days.

(21) Appl. No.: 12/482,180

(22) Filed: Jun. 10, 2009

(65) Prior Publication Data

US 2009/0312278 A1    Dec. 17, 2009

Related U.S. Application Data

(60) Provisional application No. 61/131,969, filed on Jun. 13, 2008, provisional application No. 61/099,270, filed on Sep. 23, 2008, provisional application No. 61/172,853, filed on Apr. 27, 2009.

(51) Int. Cl.
| | | |
|---|---|---|
| *A61K 31/7036* | (2006.01) | |
| *A61P 35/02* | (2006.01) | |
| *A61P 35/04* | (2006.01) | |
| *A61P 7/00* | (2006.01) | |

(52) U.S. Cl.
USPC .................................. 514/25; 514/35; 536/4.1

(58) Field of Classification Search
USPC ...................................................... 514/25, 35
See application file for complete search history.

(56) References Cited

U.S. PATENT DOCUMENTS

| | | | | |
|---|---|---|---|---|
| 4,471,057 A | 9/1984 | Koprowski et al. | ............ | 436/518 |
| 4,851,511 A | 7/1989 | Hakomori et al. | ............ | 530/387 |
| 4,859,769 A | 8/1989 | Karlsson et al. | ............ | 536/53 |
| 4,876,199 A | 10/1989 | Hakamori | ............ | 530/387 |
| 4,925,796 A | 5/1990 | Bergh et al. | ............ | 435/97 |
| 4,946,830 A | 8/1990 | Pulverer et al. | ............ | 514/23 |
| 5,143,712 A | 9/1992 | Brandley et al. | ............ | 424/1.1 |
| 5,151,360 A | 9/1992 | Handa et al. | ............ | 435/240.2 |
| 5,211,937 A | 5/1993 | Brandley et al. | ............ | 424/1.1 |
| 5,268,364 A | 12/1993 | Kojima et al. | ............ | 514/25 |
| 5,304,640 A | 4/1994 | Lasky et al. | ............ | 536/23.5 |
| 5,352,670 A | 10/1994 | Venot et al. | ............ | 514/54 |
| 5,369,096 A | 11/1994 | Yamada et al. | ............ | 514/61 |
| 5,412,123 A | 5/1995 | Rao et al. | ............ | 552/290 |
| 5,444,050 A | 8/1995 | Kogan et al. | ............ | 514/25 |
| 5,464,778 A | 11/1995 | Cummings et al. | ............ | 436/503 |
| 5,464,815 A | 11/1995 | Chamow et al. | ............ | 514/8 |
| 5,470,843 A | 11/1995 | Stahl et al. | ............ | 514/61 |
| 5,484,891 A | 1/1996 | Lasky et al. | ............ | 530/387.3 |
| 5,486,536 A | 1/1996 | Ward et al. | ............ | 514/460 |
| 5,519,008 A | 5/1996 | Rao et al. | ............ | 514/26 |
| 5,527,785 A | 6/1996 | Bevilacqua et al. | ............ | 514/56 |
| 5,538,724 A | 7/1996 | Butcher et al. | ............ | 424/152.1 |
| 5,559,103 A | 9/1996 | Gaeta et al. | ............ | 514/54 |
| 5,576,305 A | 11/1996 | Ratcliffe | ............ | 514/25 |
| 5,580,858 A | 12/1996 | Ippolito et al. | ............ | 514/25 |
| 5,580,862 A | 12/1996 | Rosen et al. | ............ | 514/61 |
| 5,589,465 A | 12/1996 | Ishida et al. | ............ | 514/25 |
| 5,604,207 A | 2/1997 | DeFrees et al. | ............ | 514/25 |
| 5,618,785 A | 4/1997 | Heavner et al. | ............ | 514/2 |
| 5,622,937 A | 4/1997 | Kogan et al. | ............ | 514/25 |
| 5,639,734 A | 6/1997 | Esko et al. | ............ | 514/25 |
| 5,646,123 A | 7/1997 | Ippolito et al. | ............ | 514/25 |
| 5,646,248 A | 7/1997 | Sawada et al. | ............ | 530/350 |
| 5,648,344 A | 7/1997 | Brandley et al. | ............ | 514/61 |
| 5,654,282 A | 8/1997 | Tang et al. | ............ | 514/25 |
| 5,654,412 A | 8/1997 | Srivastava et al. | ............ | 536/18.5 |
| 5,658,880 A | 8/1997 | Dasgupta et al. | ............ | 514/8 |
| 5,663,151 A | 9/1997 | Martel et al. | ............ | 514/25 |
| 5,679,321 A | 10/1997 | Dasgupta et al. | ............ | 424/9.1 |
| 5,679,644 A | 10/1997 | Rao et al. | ............ | 514/26 |
| 5,686,426 A | 11/1997 | Martel et al. | ............ | 514/25 |
| 5,693,621 A | 12/1997 | Toepfer et al. | ............ | 514/25 |
| 5,695,752 A | 12/1997 | Rosen et al. | ............ | 424/94.61 |
| 5,710,023 A | 1/1998 | Collins et al. | ............ | 435/69.1 |
| 5,710,123 A | 1/1998 | Heavner et al. | ............ | 514/2 |
| 5,723,583 A | 3/1998 | Seed et al. | ............ | 530/387.3 |
| 5,728,685 A | 3/1998 | Abbas et al. | ............ | 514/53 |
| 5,739,300 A | 4/1998 | Toepfer et al. | ............ | 536/4.1 |
| 5,747,463 A | 5/1998 | Marinier et al. | ............ | 514/25 |
| 5,750,508 A | 5/1998 | Dasgupta et al. | ............ | 514/25 |
| 5,753,617 A | 5/1998 | Heavner et al. | ............ | 514/9 |

(Continued)

FOREIGN PATENT DOCUMENTS

| | | |
|---|---|---|
| EP | 319253 A2 | 6/1989 |
| EP | 381310 A1 | 8/1990 |

(Continued)

OTHER PUBLICATIONS

Stevenson, J. et al "Differential metastasis inhibition by clinically relevant levels of heparins . . . " Clin. Cancer Res. (2005) vol. 11, No. 19, pp. 7003-7011.*
Vlodaysky, I. et al "Heparanase, heparin and the coagulation system . . . " Thromb. Res. (2007) vol. 120, suppl. 2, pp. S112-S120.*
Francavilla, C. et al "The functional role of cell adhesion in tumor angiogenesis" Sem. Cancer Biol. (2009) vol. 19, pp. 298-309.*
Abraham, W.M. et al., "Selectin Blockade Prevents Antigen-induced Late Bronchial Response and Airway Hyperresponsiveness in Allergic Sheep," *Am J. Respir Crit Care Med. 159*: 1205-1214, 1999.
Acord, J. et al., "A rapid microplate method for quantifying inhibition of bacterial adhesion to eukaryotic cells," *Journal of Microbiological Methods 60*: 55-62, 2005.

(Continued)

*Primary Examiner* — Leigh Maier
(74) *Attorney, Agent, or Firm* — Ropes & Gray LLP

(57) ABSTRACT

Methods and medicaments therefor are provided for the treatment of cancers of the blood or a complication therewith in an individual. More specifically, the use of particular glycomimetics for the treatment is described. Methods and medicaments therefor are also provided without regard to cancer type for reducing in an individual the myeloablative bone marrow toxicities of chemotherapy.

7 Claims, 13 Drawing Sheets

(56) References Cited

U.S. PATENT DOCUMENTS

| | | |
|---|---|---|
| 5,753,631 A | 5/1998 | Paulson et al. .................. 514/25 |
| 5,763,413 A | 6/1998 | Numata et al. .................. 514/25 |
| 5,763,582 A | 6/1998 | Rao et al. ......................... 536/5 |
| 5,789,385 A | 8/1998 | Anderson et al. ............... 514/25 |
| 5,789,573 A | 8/1998 | Baker et al. .................. 536/24.5 |
| 5,795,958 A | 8/1998 | Rao et al. ....................... 530/331 |
| 5,811,404 A | 9/1998 | De Frees et al. ................ 514/25 |
| 5,811,405 A | 9/1998 | Toepfer et al. ................. 514/25 |
| 5,817,742 A | 10/1998 | Toepfer et al. ................. 528/328 |
| 5,827,817 A | 10/1998 | Larsen et al. ...................... 514/2 |
| 5,827,837 A | 10/1998 | Bevilacqua et al. ........... 514/103 |
| 5,830,871 A | 11/1998 | Wong et al. ..................... 514/23 |
| 5,837,689 A | 11/1998 | Anderson et al. ............... 514/25 |
| 5,837,690 A | 11/1998 | Rao et al. ......................... 514/26 |
| 5,840,679 A | 11/1998 | Larsen et al. ...................... 514/8 |
| 5,854,218 A | 12/1998 | DeFrees ........................... 514/25 |
| 5,858,983 A | 1/1999 | Seed et al. ....................... 514/23 |
| 5,858,994 A | 1/1999 | Kretzschmar et al. .......... 514/62 |
| 5,880,091 A | 3/1999 | Cummings et al. ............... 514/8 |
| 5,916,910 A | 6/1999 | Lai .................................. 514/423 |
| 5,919,768 A | 7/1999 | Korgan et al. ................... 514/25 |
| 5,919,769 A | 7/1999 | Tsukida et al. .................. 514/25 |
| 5,962,422 A | 10/1999 | Nagy et al. ....................... 514/25 |
| 5,976,540 A | 11/1999 | Rittershaus et al. ......... 424/184.1 |
| 5,977,080 A | 11/1999 | Rosen et al. ..................... 514/25 |
| 5,985,852 A | 11/1999 | Nagy et al. ....................... 514/54 |
| 5,994,402 A | 11/1999 | Rotstein et al. ................ 514/547 |
| 6,001,819 A | 12/1999 | Simon et al. ..................... 514/54 |
| 6,001,988 A | 12/1999 | Parma et al. ................... 536/24.3 |
| 6,033,665 A | 3/2000 | Yednock et al. ............. 424/130.1 |
| 6,037,333 A | 3/2000 | Panjwani ......................... 514/62 |
| 6,110,897 A | 8/2000 | Unverzagt et al. .............. 514/25 |
| 6,111,065 A | 8/2000 | Heavner et al. ............... 530/300 |
| 6,120,751 A | 9/2000 | Unger ........................... 424/9.51 |
| 6,121,233 A | 9/2000 | Magnani et al. .................. 514/8 |
| 6,124,267 A | 9/2000 | Mc Ever et al. ................. 514/25 |
| 6,133,239 A | 10/2000 | Handa et al. ..................... 514/25 |
| 6,133,240 A | 10/2000 | Taylor et al. ..................... 514/25 |
| 6,136,790 A | 10/2000 | Toepfer et al. ................... 514/25 |
| 6,169,077 B1 | 1/2001 | Oehrlein ........................... 514/25 |
| 6,177,547 B1 | 1/2001 | Cummings et al. ........ 530/388.22 |
| 6,187,754 B1 | 2/2001 | Oehrlein ........................... 514/25 |
| 6,193,973 B1 | 2/2001 | Tuttle ........................... 424/195.1 |
| 6,193,979 B1 | 2/2001 | Rittershaus et al. ....... 424/195.11 |
| 6,197,752 B1 | 3/2001 | Schmidt et al. .................. 514/23 |
| 6,225,071 B1 | 5/2001 | Cummings et al. ........... 435/7.24 |
| 6,235,309 B1 | 5/2001 | Nagy et al. ..................... 424/450 |
| 6,280,932 B1 | 8/2001 | Parma et al. ...................... 435/6 |
| 6,309,639 B1 | 10/2001 | Cummings et al. .......... 424/143.1 |
| 6,387,884 B1 | 5/2002 | Magnani et al. ................. 514/25 |
| 6,391,857 B1 | 5/2002 | Magnani et al. ................. 514/25 |
| 6,407,135 B1 | 6/2002 | Lai et al. ........................ 514/423 |
| 6,465,434 B1 | 10/2002 | Magnani et al. ................. 514/23 |
| 6,492,332 B1 | 12/2002 | Demopulos et al. ............. 514/12 |
| 6,503,885 B1 | 1/2003 | Kiso et al. ........................ 514/25 |
| 6,528,487 B1 | 3/2003 | Heavner et al. ................. 514/13 |
| 7,060,685 B2 | 6/2006 | Magnani et al. ................. 514/25 |
| 7,728,117 B2 | 6/2010 | Magnani et al. | |
| 7,741,312 B2 | 6/2010 | Magnani et al. | |
| 7,989,601 B2 | 8/2011 | Magnani et al. | |
| 8,039,442 B2 | 10/2011 | Magnani et al. | |
| 2001/0046970 A1 | 11/2001 | Nagy et al. ....................... 514/53 |
| 2001/0051370 A1 | 12/2001 | Bistrup et al. .................. 435/193 |
| 2002/0026033 A1 | 2/2002 | Cummings et al. ............ 530/322 |
| 2002/0028205 A1 | 3/2002 | Holgersson et al. ........ 424/184.1 |
| 2002/0031508 A1 | 3/2002 | Wagner et al. ............... 424/94.63 |
| 2002/0040008 A1 | 4/2002 | Wagner et al. ................... 514/41 |
| 2002/0132220 A1 | 9/2002 | Berens et al. .................. 435/1.1 |
| 2002/0164336 A1 | 11/2002 | Harrison et al. ............. 424/146.1 |
| 2002/0164748 A1 | 11/2002 | Bistrup et al. .................. 435/193 |
| 2002/0168366 A1 | 11/2002 | Stewart et al. .............. 424/146.1 |
| 2003/0012787 A1 | 1/2003 | Ashkenazi et al. ........ 424/145.1 |
| 2003/0012790 A1 | 1/2003 | Ashkenazi et al. ........ 424/178.1 |
| 2003/0018181 A1 | 1/2003 | Larsen et al. ................. 536/23.4 |
| 2003/0039683 A1 | 2/2003 | Cantrell et al. ............... 424/450 |
| 2004/0219158 A1 | 11/2004 | Magnani | |
| 2005/0112124 A1 | 5/2005 | Frenette et al. | |
| 2005/0187171 A1 | 8/2005 | Magnani et al. ................. 514/43 |
| 2006/0217303 A1 | 9/2006 | Kriegler | |
| 2006/0287253 A1 | 12/2006 | Kriegler et al. | |
| 2007/0054870 A1 | 3/2007 | Magnani et al. ................. 514/35 |
| 2008/0112955 A1 | 5/2008 | Embury et al. | |
| 2008/0200406 A1 | 8/2008 | Magnani | |

FOREIGN PATENT DOCUMENTS

| | | |
|---|---|---|
| EP | 408859 B1 | 8/1995 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 99/42130 | 8/1999 |
| WO | WO 99/43353 | 9/1999 |
| WO | WO 99/43356 | 9/1999 |
| WO | WO 01/89564 | 11/2001 |
| WO | WO 02/22820 | 3/2002 |
| WO | WO 02/062810 | 8/2002 |
| WO | WO 03/088980 | 10/2003 |
| WO | WO 03/097658 | 11/2003 |
| WO | WO 2004/004636 | 1/2004 |
| WO | WO 2004/058304 | 7/2004 |
| WO | WO 2005/051920 | 6/2005 |
| WO | WO 2005/054264 | 6/2005 |
| WO | WO 2005/116088 | 12/2005 |
| WO | WO 2006/127906 | 11/2006 |
| WO | WO 2007/028050 | 3/2007 |
| WO | WO 2009/011889 | 1/2009 |
| WO | WO 2009/126556 | 10/2009 |

OTHER PUBLICATIONS

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem.* 266 (32):21537-21547, 1991.

Bänteli, R. et al., "Potent E-Selectin Antagonists," Helvetica Chimica Acta 83(11): 2893-2907, 2000.

Belcher, J.D. et al., "Activated monocytes in sickle cell disease: potential role in the activation of vascular endothelium and vaso-occlusion," Blood, 96(7): 2451-2459, Oct. 1, 2000.

Belcher, J.D. et al., "Inflammatory Response in Transgenic Mouse Models of Human Sickle Cell Anemia," Abstract #2574, Blood, 96(11): 600a, Nov. 16, 2000.

Berg et al., "A Carbohydrate Domain Common to Both Sialyl Lea and Sialyl Lex Is Recognized by the Endothelial Cell Leukocyte Adhesion Molecule ELAM-1," J. Biol. Chem. 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.

Bird and Kimber, "Oligosaccharides Containing Fucose Linked α(1-3) and α(1-4) to N-Acetylglucosamine Cause Decompaction of Mouse Morulae," Devel. Biol. 104:449-460, 1984.

Blanc-Muesser, et al., "Syntheses Stereoselective de 1-Thioglycosides," Carbohydrate Research 67:305-328, 1978.

Bock, K. et al., "Conformations in Solution of α,α-Trehalose, α-D-Glucopyranosyl α-D-Mannopyranoside, and Their 1-Thioglycosyl Analogs, and a Tentative Correlation of Their Behaviour with Respect to the Enzyme Trehalase," European Journal of Biochemistry 131:595-600, 1983.

Bowen et al., "Characterization of a Human Homologue of the Murine Peripheral Lymph Node Homing Receptor," Journal of Cell Biology 109:421-427, 1989.

Brandley et al., "Carbohydrate Ligands of LEC Cell Adhesion Molecules," Cell 63:861-863, 1990.

Broquet et al., "Effect of Desipramine on a Glycoprotein Sialyltransferase Activity in C6 Cultured Glioma Cells," J. Neurochem. 54:388-394, 1990.

Cao, X. et al., "Defective Lymphoid Development in Mice Lacking Expression of the Common Cytokine Receptor γ Chain," *Immunity* 2:223-238, Mar. 1995.

Ceder, O. et al., "On the Absolute Configuration of 3-Cyclohexene-1-carboxylic Acid," Acta Chemica Scandinavica 24(8):2693-2698, 1970.

Chemical Abstracts (STN), Accession No. 1997:5843307, Jul. 8, 1997.

Childs et al., "High-molecular-weight glycoproteins are the major carriers of the carbohydrate differentiation antigens I, i and SSEA-1 of mouse teratocarcinoma cells," Biochem. J. 215:491-503, 1983.

Christianson, S.W. et al., "Enhanced Human $CD^+$ T Cell Engraftment in $β_2$-Microglobulin-Deficient NOD-*scid* Mice," *The Journal of Immunology* 158:3578-3586, 1997.

Cleophax, J. et al., "A Chiral Synthesis of D-(+)-2,6-Dideoxystreptamine and Its Microbial Incorporation into Novel Antibiotics," Journal of the American Chemical Society, 98(22):7110-7112, Oct. 27, 1976.

Corral et al., "Requirements for Sialic Acid on Neutrophils in a GMP-140 (PADGEM) Mediated Adhesive Interaction with Activated Platelets," Biochem. Biophys. Res. Commun. 172:1349-1356, 1990.

Datta and Takayama, "Isolation and purification of trehalose 6-mono- and 6,6'-di-corynomycolates from *Cornyebacterium matruchotii*. Structural characterization of 1H NMR," Carbohydrate Research 245: 151-158, 1993.

Duijvestijn et al., "High Endothelial Differentiation in Human Lymphoid and Inflammatory Tissues Defined by Monoclonal Antibody HECA-452," Am. J. Path. 130:147-155, 1988.

Dupré, B. et al., "Glycomimetic Selectin Inhibitors: (α-D-Mannopyranosyloxy)methylbiphenyls," Bioorganic & Medicinal Chemistry Letters 6(5): 569-572, 1996.

Edgington, "How Sweet It Is: Selectin-Mediating Drugs," Biotechnology 10: 383-389, 1992.

Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.

Eggens et al., "Specific Interaction between Lex and Lex Determinants. A Possible Basis for Cell Recognition in Preimplantation Embryos and in Embryonal Carcinoma Cells," J. Biol. Chem. 264(16):9476-9484, 1989.

Embury, S.H. et al., "The contribution of endothelial cell P-selectin to the microvascular flow of mouse sickle erythrocytes in vivo," Blood, 104(10): 3378-3385, Nov. 15, 2004.

Ernst and Oehrlein, "Substrate and donor specificity of glycosyl transferases," Glycoconjugate Journal 16: 161-170, 1999.

Fenderson, B. et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.

Fenderson et al., "Coordinate Expression of X and Y Haptens during Murine Embryogenesis," Devel. Biol. 114:12-21, 1986.

Fenderson et al., "The blood group I antigen defined by monoclonal antibody C6 is a marker of early mesoderm during murine embryogenesis," Differentiation 38:124-133, 1988.

Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.

Fukushi et al., "Novel Fucolipids Accumulating in Human Adenocarcinoma. III. A Hybridoma Antibody (FH6) Defining a Human Cancer-Associated Difucoganglioside (VI3NeuAcV3III3Fuc2nLc6)," J. Biol. Chem. 259(16):10511-10517, 1984.

Gabius et al., "Endogenous Tumor Lectins: Overview and Perspectives," Anticancer Res. 6:573-578, 1986.

Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.

Gallatin et al., "A cell-surface molecule involved in organ-specific homing of lymphocytes," Nature 304:30-34, 1983.

Gooi et al., "Stage-specific embryonic antigen involves α 1 → 3 fucosylated type 2 blood group chains," Nature 292:156-158, 1981.

Hakomori et al., "Novel Fucolipids Accumulating in Human Adenocarcinoma. I. Glycolipids With Di- or Trifucosylated Type 2 Chain," J. Biol. Chem. 259(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.

Hakomori S., "Aberrant Glycosylation in Cancer Cell Membranes as Focused on Glycolipids: Overview and Perspectives," Cancer Res. 45:2405-2414, 1985.

Handa et al., "Selectin GMP-140 (CD62; PADGEM) Binds to Sialosyl-Lea and Sialosyl-Lex, and Sulfated Glycans Modulate this Binding," Biochemical and Biophysical Research Communication 181(3):1223-1230, 1991.

Hansson and Zopf, "Biosynthesis of the Cancer-associated Sialyl-Lea Antigen," Journal of Biological Chemistry 260(16):9388-9392, 1985.

Harlan, John M., "Introduction: anti-adhesion therapy in sickle cell disease," Blood, 95(2): 365-367, Jan. 15, 2000.

Hasegawa et al., "Synthesis of deoxy-L-fucose-containing sialyl Lewis X ganglioside analogues," Carbohydrate Research 257: 67-80, 1994.

Hasegawa et al., "Synthesis of sialyl Lewis X ganglioside analogues containing modified L-fucose residues," Carbohydrate Research 274: 165-181, 1995.

Hebbel, R.P., "Blockade of Adhesion of Sickle Cells to Endothelium by Monoclonal Antibodies," The New England Journal of Medicine, 342(25): 1910-1912, Jun. 22, 2000.

Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

Huse et al., "Generation of a Large Combinatorial Library of the Immunoglobulin Repertoire in Phage Lambda," Science 246:1275-1281, 1989.

Huwe, C.M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.

Hynes, R., "Integrins: A Family of Cell Surface Receptors," Cell 48:549-554, 1987.

Inwald, D.P. et al., "Platelet and leucocyte activation in childhood sickle cell disease: association with nocturnal hypoxaemia," British Journal of Haemotology, 111(2): 474-481, Nov. 2000.

Ishikawa, F. et al., "Chemotherapy-resistant human AML stem cells home to and engraft within the bone-marrow endosteal region," *Nature Biotechnology 25* (11):1315-1321, Nov. 2007.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.

Itai, S. et al., "Differentiation-dependent Expression of I and Sialyl I Antigens in the Developing Lung of Human Embryos and in Lung Cancers," Cancer Research 50: 7603-7611, 1990.

Jeffrey et al., "Affinity Chromatography of Carbohydrate-Specific Immunoglobulins: Coupling of Oligosaccharides to Sepharose ," Biochem. Biophys. Res. Commun. 62:608-613, 1975.

Jentsch, K.D. et al., "Inhibition of Human Immunodeficiency Virus Type I Reverse Transcriptase by Suramin-related Compounds," The Journal of General Virology 68(8): 2183-2192, 1987.

Kaila, N. et al., "Design and Synthesis of Sialyl Lewis Mimics as E- and P-Selectin Inhibitors," Medicinal Research Reviews, 22(6):566-601, 2002.

Kaila, N. et al., "β-C-Mannosides as Selectin Inhibtors," Journal of Medicinal Chemistry 45(8):1563-1566, 2002.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.

Kannagi et al., "Stage-specific embryonic antigens (SSEA-3 and -4) are epitopes of a unique globo-series ganglioside isolated from human teratocarcinoma cells," Embo J. 2(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.

Kaul, D.K. et al., "Hypoxia/reoxygenation causes inflammatory response in transgenic sickle mice but not in normal mice," The Journal of Clinical Investigation, 106(3): 411-420, Aug. 2000.

Kitagawa et al., "Characterization of Mucin-Type Oligosaccharides With the Sialyl-Lea Structure From Human Colorectal Adenocarcinoma Cells," Biochem. Biophys. Res. Commun. 178(3):1429-1436, 1991.

Kitagawa et al., "Immunoaffinity Isolation of a Sialyl-Lea Oligosaccharide from Human Milk," J. Biochem. 104:591-594, 1988.

Kneuer, C. et al., "Selectins—potential pharmacological targets?" Drug Discovery Today, 11(21/22): 1034-1040, Nov. 2006.

Kogan, T.P. et al., "Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.

Kogan, T.P. et al., "Novel Synthetic Inhibitors of Selectin-Mediated Cell Adhesion: Synthesis of 1,6-Bis[3-(3-carboxymethylphenyl)-r-(2-α-D-monnopyranosyloxy)phenyl]hexane (TBC1269)," J. Med. Chem 41:1099-1111, 1998.

Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," J. Med. Chem. 38: 4976-4984, Dec. 22, 1995.

Köhler and Milstein, "Continuous cultures of fused cells secreting antibody of predefined specificity," Nature 256:495-497, 1975.

Köhler and Milstein, "Derivation of specific antibody-producing tissue culture and tumor lines by cell fusion," Eur. J. Immunol. 6:511-519, 1976.

Kojima and Hakomori, "Specific Interaction between Gangliotriaosylceramide (Gg3) and Sialosyllactosylceramide (GM3) as a Basis for Specific Cellular Recognition between Lymphoma and Melanoma Cells," J. Biol. Chem. 264(34):20159-20162, 1989.

Kolb, H.C. et al., "Development of Tools for the Design of Selectin Antagonists," Chem. Eur. J. 3(10):1571-1578, 1997.

Kolb, H.C. et al., "Recent progress in the glycodrug area," Pure & Applied Chemistry 69(9):1879-1884, 1997.

Koprowski et al., "Colorectal Carcinoma Antigens Detected by Hybridoma Antibodies," Somatic Cell Genetics 5(6):957-972, 1979.

Kuzuoka, "Antitumor activity of murine monoclonal antibody NCC-ST-421," Chem. Ab. 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→•) Structural Element Revealed by 500-Mhz H NMR Spectroscopy," Journal of Biological Chemistry 259(14):9051-9058, 1984.

Larsen et al., PADGEM-Dependent Adhesion of Platelets to Monocytes and Neutrophils Is Mediated by a Lineage-Specific Carbohydrate, LNF III (CD15), Cell 63:467-474, 1990.

Lindenberg et al., "Carbohydrate binding properties of mouse embryos," J. Reprod. Fert. 89:431-439, 1990.

Lipartiti et al., "Monosialoganglioside GM1 Reduces NMDA Neurotoxicity in Neonatal Rat Brain," Experimental Neurology 113:301-305, 1991.

Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.

Lowe et al., "ELAM-1-Dependent Cell Adhesion to Vascular Endothelium Determined by a Transfected Human Fucosyltransferase cDNA," Cell 63:475-484, 1990.

Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.

Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.

Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.

Magnani, J., "Carbohydrate Sequences Detected by Murine Monoclonal Antibodies," Chemistry and Physics of Lipids 42:65-74, 1986.

Magnani, J., "Potent Glycomimetic Inhibitors of the Adhesion Molecule, Pa-IIL, for the Bacterial Pathogen, Pseudomonas auroginosa," Glycobiology 13(11): 854, Abstract No. 104, Oct. 2003.

Matsui, N.M. et al., "Heparin inhibits the flow adhesion of sickle red blood cells to P-selectin," Blood, 100(10): 3790-3796, Nov. 15, 2002.

Matsui, N.M. et al., "P-selectin mediates the adhesion of sickle erythrocytes to the endothelium," Blood, 98(6): 1955-1962, Sep. 15, 2001.

Matsui, N.M. et al., "The Novel Adhesion of Erythrocytes to P-Selectin in Sickle Cell Disease," Abstract #2575, Blood, 96(11): 600a, Nov. 16, 2000.

Mulligan and Berg, "Selection for animal cells that express the Escherichia coli gene coding for xanthine-gunine phosphoribosyltransferase," Proc. Natl. Acad. Sci. USA 78:2072-2076, 1981.

Nagel, R.L., "A Knockout of a Transgenic Mouse—Animal Models of Sickle Cell Anemia," The New England Journal of Medicine, 339(3):194-195, Jul. 16, 1998.

Natarajan, M. et al., "Adhesion of Sickle Red Blood Cells and Damage to Interleukin-1β Stimulated Endothelial Cells Under Flow in Vitro," Blood, 87(11): 4845-4852, Jun. 1, 1996.

Nicolaou et al., "Total Synthesis of the Tumor-Associated Lex Family of Glycosphingolipids," J. Amer. Chem. Soc. 112:3693-3695, 1990.

Nudelman et al., "Novel Fucolipids of Human Adenocarcinoma: Disialosyl Lea Antigen (III4FucIII6NeuAcIV3NeuAcLc4) of Human Colonic Adenocarcinoma and the Monoclonal Antibody (FH7) Defining This Structure," J. Biol. Chem. 261:5487-5495, 1986.

Öhrlein, R., "Carbohydrates and Derivatives as Potential Drug Candidates with Emphasis on the Selectin and Linear-B Area," Mini Reviews in Medicinal Chemistry 1: 349-361, 2001.

Palcic et al., "Enzymic Synthesis of Oligosaccharides Terminating in the Tumor-Associated Sialyl-Lewis-a Determinant," Carbohydr. Res. 190:1-11, 1989.

Palcic et al., "Regulation of N-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," J. Biol. Chem. 265:6759-6769, 1990.

Palcic et al., "A Bisubstrate Analog Inhibitor for α(1→2)-Fucosyltransferase," J. Biol. Chem. 264:17174-17181, 1989.

Palma-Vargas, J.M. et al., "Small-Molecule Selectin Inhibitor Protects Against Liver Inflammatory Response After Ischemia and Reperfusion," J. Am. Coll. Surg. 185: 365-372, 1997.

Patton, J.T. et al., "GMI-1070: a Small, Glycomimetic, Pan-selectin Antagonist that Improves Blood Flow and Inhibits Blood Cell Adhesion in Sickle Mice," Glyco XIX, Gaithersburg, Maryland, Sep. 2, 2005. Available from http://ww.glycomimetics.com/library. Accessed Jun. 10, 2009.

Perret, S. et al., "Structural basis for the interaction between human milk oligosaccharides and the bacterial lectin PA-IIL of Pseudomonas aeruginosa," Biochem. J. 389: 325-332, 2005.

Phillips et al., "ELAM-1 Mediates Cell Adhesion by Recognition of a Carbohydrate Ligand, Sialyl-Lex," Science 250:1130-1132, 1990.

Picker et al., "The Neutrophil Selectin LECAM-1 Presents Carbohydrate Ligands to the Vascular Selectins ELAM-1 and GMP-140," Cell 66:921-933, 1991.

Prokazova et al., "Sialylated lactosylceramides. Possible inducers of non-specific immunosuppression and atherosclerotic lesions," European Journal of Biochemistry 172:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.

Rice and Bevilacqua, "An Inducible Endothelial Cell Surface Glycoprotein Mediates Melanoma Adhesion," Science 246:1303-1306, 1989.

Ruoslahti and Pierschbacher, "New Perspectives in Cell Adhesion: RGD and Integrins," Science 238:491-497, 1987.

Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.

Sastry et al., "Cloning of the immunological repertoire in Escherichia coli for generation of monoclonal catalytic antibodies: Construction of a heavy chain variable region-specific cDNA library," Proc. Natl. Acad. Sci. USA 86:5728-5732, 1989.

Scharfman, A. et al., "Pseudomonas aeruginosa binds to neoglycoconjugates bearing mucin carbohydrate determinants and predominantly to sialyl-Lewis x conjugates," Glycobiology 9(8): 757-764, 1999.

Scharfman, A. et al., "Recognition of Lewis x Derivatives Present on Mucins by Flagellar Components of Pseudomonas aeruginosa," Infection and Immunity 69(9): 5243-5248, Sep. 2001.

Shitara et al., "Application of Anti-Sialyl Lea Monoclonal antibody, KM231, for Immunotherapy of Cancer," Anticancer Res. 11:2003-2014, 1991.

Siuzdak et al., "Examination of the Sialyl Lewis X—Calcium Complex by Electrospray Mass Spectrometry," Bioorganic & Medicinal Chemistry Letters 4(24): 2863-2866, 1994.

Solovey, A. et al., "Circulating Activated Endothelial Cells in Sickle Cell Anemia," The New England Journal of Medicine, 337(22): 1584-1590, Nov. 27, 1997.

Solovey, AA., et al., "Modulation of endothelial cell activation in sickle cell disease: a pilot study," Blood, 97(7): 1937-1941, Apr. 1, 2001.

Sprengard, U. et al., "Synthesis and Biological Activity of Novel Sialyl-LewisX Conjugates," Bioorganic & Medicinal Chemistry Letters 6(5): 509-514, 1996.

Stanley and Atkinson, "The LEC11 Chinese Hamster Ovary Mutant Synthesizes N-Linked Carbohydrates Containing Sialylated, Fucosylated Lactosamine Units. Analysis by One-and Two-Dimensional H NMR Spectroscopy," J. Biol. Chem. 263(23):11374-11381, 1988.

Stephens and Cockett, "The construction of highly efficient and versatile set of mammalian expression vectors," Nucleic Acids Research. 17:7110, 1989.

Streeter et al., "Immunohistologic and Functional Characterization of a Vascular Addressin Involved in Lymphocyte Homing into Peripheral Lymph Nodes," Journal of Cell Biology 107: 1853-1862, 1988.

Stroud et al., "Extended Type 1 Chain Glycosphingolipids: Dimeric Lea (III4V4Fuc2Lc6) as Human Tumor-associated Antigen," J. Biol. Chem. 266(13):8439-8446, 1991.

Svenson and Lindberg, "Coupling of Acid Labile Salmonella Specific Oligosaccharides to Macromolecular Carriers," J. Immunol. Meth. 25:323-335, 1979.

Takada et al., "Adhesion of Human Cancer Cells to Vascular Endothelium Mediated by a Carbohydrate Antigen, Sialyl Lewis A1," Biochem. Biophys. Res. Commun. 179(2):713-719, 1991.

Takeichi, M., "Cadherins: a molecular family essential for selective cell-cell adhesion and animal morphogenesis," Trends Genet. 3(8):213-217, 1987.

Thoma, G. et al., "A readily Available, Highly Potent E-Selectin Antagonist," Angew. Chem. Int. Ed. 40(19): 3644-3647, 2001.

Thoma, G. et al., "Preorganization of the Bioactive Conformation of Sialyl LewisX Analogues Correlates with Their Affinity to E-Selectin," Angew. Chem. Int. Ed. 40(10): 1941-1945, 2001.

Thoma, G. et al., "Synthesis and Biological Evaluation of a Potent E-Selectin Antagonist," J. Med. Chem., 42: 4909-4913, 1999.

Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.

Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.

Turhan, A. et al., "Primary role for adherent leukocytes in sickle cell vascular occlusion: A new paradigm," Proceedings of the National Academy of Sciences, 99(5): 3047-3051, Mar. 5, 2002.

Tyrrell et al., "Structural requirements for the carbohydrate ligand of E-selectin," Proc. Natl. Acad. Sci. USA 88:10372-10376, 1991.

Waldmann, H. et al., "Synthesis of 2-Acetamindo-2-Deoxyglucosylasparagine Glyco-Tripeptide and—Pentapeptides by Selective C- and N-Terminal Elongation of the Peptide Chain," Carbohydrate Research 196: 75-93, 1990.

Walz et al., "Recognition by ELAM-1 of the Sialyl-Lex Determinant on Myeloid and Tumor Cells," Science 250:1132-1135, 1990.

Ward and Mulligan, "Blocking of adhesion molecules in vivo as anti-inflammatory therapy," Immunology 1: 165-171, 1994.

Whisler and Yates, "Regulation of Lymphocyte Responses by Human Gangliosides. I. Characteristics of Inhibitory Effects and the Induction of Impaired Activation," Journal of Immunology 125(5):2106-2111, 1980.

Yamazaki, F. et al., "Syntheisis of an appropriately protected core glycotetraoside, a key intermediate for the synthesis of 'bisected' complex-type glycans of a glycoprotein," Carbohydrate Research 201: 15-30, 1990.

Zhou et al., "The Selectin GMP-140 Binds to Sialylated, Fucosylated Lactosaminoglycans on Both Myeloid and Nonmyeloid Cells," Journal of Cell Biology 115(2):557-564, 1991.

Zopf et al., "Affinity Purification of Antibodies Using Oligosaccharide-Phenethylamine Derivatives Coupled to Sepharose," Meth. Enzymol. 50:171-175, 1978.

Bastin, R. et al, "Salt Selection and Optimisation Procedures for Pharmaceutical New Chemical Entities" Organic Process Research & Development (2000), vol. 4, pp. 427-435.

Bjercke, "Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI, 018.

Ernst B. et al., "Design and Synthesis of E-Selectin Antagonists," Chimia (2001), vol. 55, No. 4, pp. 268-274.

Lee et al., "A new method of sequencing linear oligosaccharides on gels using charged, fluorescent conjugates" Carbohydrate Research, vol. 214, 1991, pp. 155-168, XP000226749.

Li, B., et al., "Delaying Acute Graft-Versus-Host Disease in Mouse Bone Marrow Transplantation by Treating Donor Cells with Antibodies Directed at L-Selectin and α4-Integrin Prior to Infusion," Scandinavian Journal of Immunology, 59:464-468, 2004.

Payre, et al., "Chemoenzymatische Synthese eines zweifach modifizierten Pentasaccharids als Substrat für einen α-Amylase-Assay durch Fluoreszenz-löschung" Angew. Chem., vol. 107, No. 11, 1995, pp. 1361-1364.

Titz, A. et al., "Mimetics of Sialyl Lewis$^x$: The Pre-Organization of the Carboxylic Acid is Essential for Binding to Selectins", Chimia (2007), vol. 61, pp. 194-197.

* cited by examiner

Compound #2 inhibits SDF-1 induced Transendothelial Migration of MM cells

TREATMENT OF CANCERS OF THE BLOOD USING SELECTED GLYCOMIMETIC COMPOUNDS

CROSS REFERENCE TO RELATED APPLICATIONS

This application claims the benefit under 35 U.S.C. §119(e) of U.S. Provisional Patent Application No. 61/131,969 filed Jun. 13, 2008, U.S. Provisional Patent Application No. 61/099,270 filed Sep. 23, 2008 and U.S. Provisional Patent Application No. 61/172,853 filed Apr. 27, 2009; which applications are incorporated herein by reference in their entirety.

BACKGROUND

1. Technical Field

The present invention relates generally to methods for treating cancers of the blood or complications associated therewith, and for the reduction of a myeloablative bone marrow toxicity of chemotherapy without regard for cancer type, and more specifically to the use of particular glycomimetics for the treatment.

2. Description of the Related Art

One of the groups of cancers is cancers of the blood. Such cancer group includes hematological malignancies. Acute myelogenous leukemia is an example of a cancer of the blood.

Acute myelogenous leukemia (also known as acute myeloid leukemia or AML) is a cancer of white blood cells, and in particular the myeloid line. It appears that AML arises from a single progenitor cell which has undergone genetic transformation to an abnormal cell with the ability to proliferate rapidly. These abnormal immature myeloid cells accumulate in the bone marrow. This accumulation in the bone marrow interferes with the production of normal blood cells, including a reduction in red blood cells, platelets and neutrophils. Eventually the bone marrow stops working correctly.

AML is one of the most common types of leukemia among adults, and the most common acute leukemia affecting adults. In the U.S. alone, there are approximately 12,000 new cases each year. The incidence of AML is expected to increase as the population ages. In addition, in the U.S., about 11% of the cases of leukemia in childhood are AML. Chemotherapy is generally used to treat AML. Only a minority of patients are cured with current therapy.

Chemotherapy has a number of deleterious side effects. One of the side effects is myeloablative bone marrow toxicities. Bone marrow is the tissue that fills the inside of some bones. Examples of such bones are sternum, hip, femur and humerus. Bone marrow contains stem cells that develop into several types of blood cells: erythrocytes (red blood cells), leukocytes (white blood cells) and thrombocytes (platelets). Cells in the bone marrow are susceptible to the effects of chemotherapy due to their rapid rate of division. Bone marrow is prevented by chemotherapeutic agents from forming new blood cells. With time after exposure to a chemotherapeutic agent, counts of the blood cells will fall at various rates, depending upon the particular type of cell as their average life spans differ. Low white blood cell count, for example, makes an individual more susceptible to infection. Low red blood cell count, for example, causes an individual to be fatigued. Low platelet count, for example, impairs an individual's ability to make a blood clot.

Accordingly, there is a need in the art for the treatment of cancers of the blood, including acute myelogenous leukemia, or complications associated therewith, and for the reduction of a myeloablative bone marrow toxicity of chemotherapy. The present invention fulfills these needs and further provides other related advantages.

BRIEF SUMMARY

Briefly stated, methods for treating cancers of the blood or the complications associated therewith, and methods without regard for cancer type for the reduction of a myeloablative bone marrow toxicity of chemotherapy, are provided. In the present invention, the compounds used for treatment and for reduction comprise, or consist of, a particular glycomimetic. Such a compound may be combined with a pharmaceutically acceptable carrier or diluent to form a pharmaceutical composition.

In one embodiment, the present invention provides a method for the treatment of a cancer of the blood or a complication associated therewith in an individual who is in need thereof, comprising administering to the individual a compound in an amount effective for treatment, the compound with the formula:

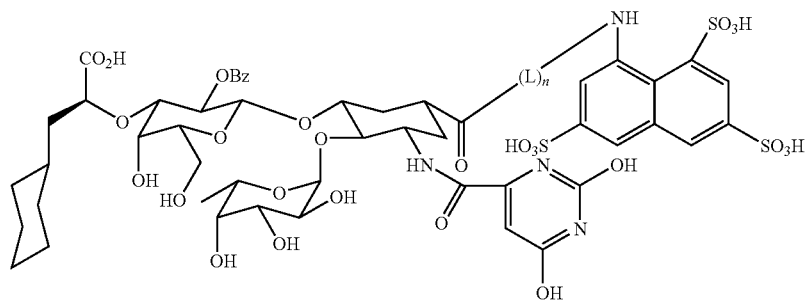

wherein
L=linker group; and
n=0-1.

In an embodiment, the present invention provides a method for reducing a myeloablative bone marrow toxicity of chemotherapy in an individual who is in need thereof, comprising administering to the individual a compound in an amount effective for the reduction, the compound with the formula:

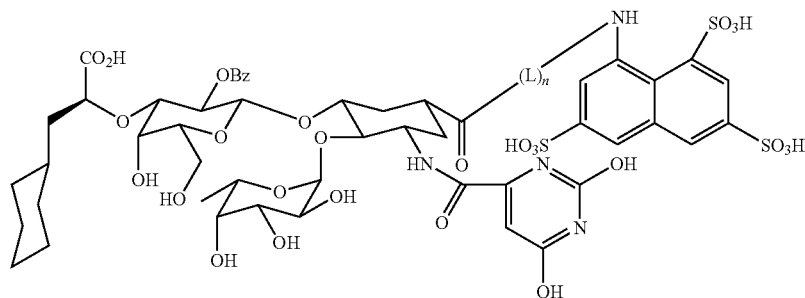

wherein
L=linker group; and
n=0-1.

In an embodiment, the above compounds are in combination with a pharmaceutically acceptable carrier or diluent.

In an embodiment, the cancer of the blood is acute myelogenous leukemia (AML).

In other embodiments, the above compounds or compositions thereof may be used in the manufacture of a medicament, for any of the uses recited herein.

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1:
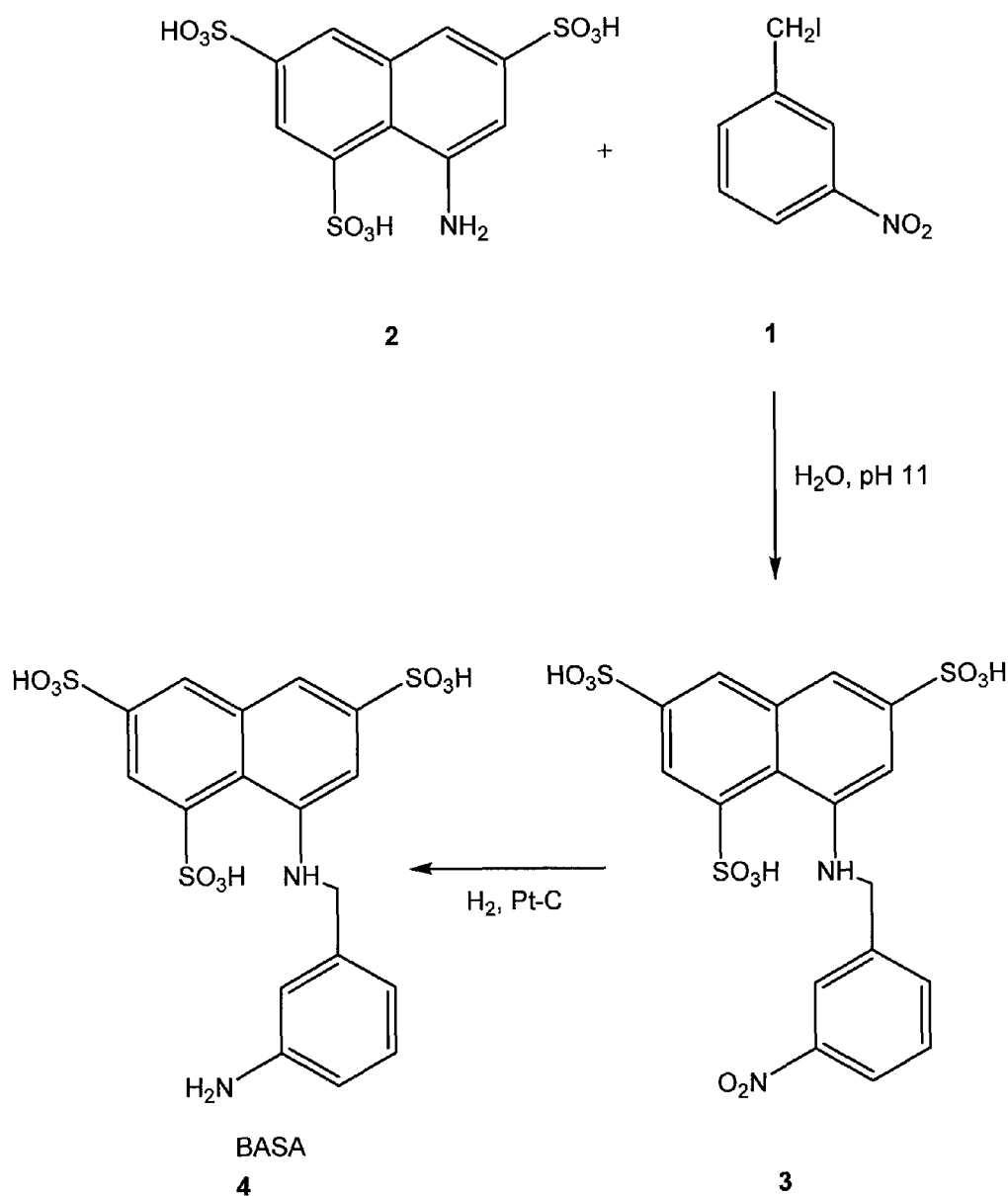
FIG. 1 is a diagram illustrating the synthesis of a component of Compound #1.

As noted above, the present invention provides methods for the treatment of cancers of the blood or a complication associated therewith in an individual, and methods without regard for cancer type for the reduction of myeloablative bone marrow toxicities of chemotherapy.

Compounds useful in the compositions (including medicaments) and methods of the present invention include embodiments with the formula:

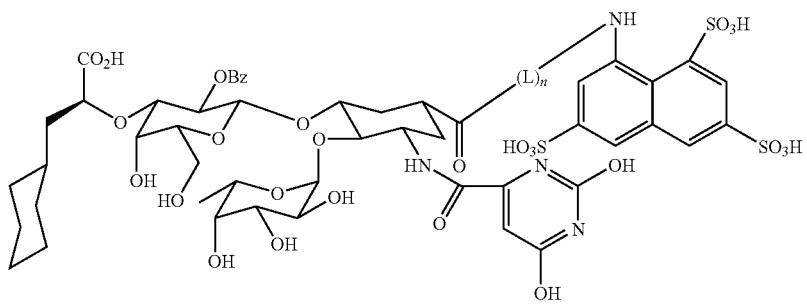

In the above formula, "L" represents a linker. There may be no linkers present (i.e., "n" is 0) or a linker may be present (i.e., "n" is 1). Where no linker is present, the compound is with the formula:

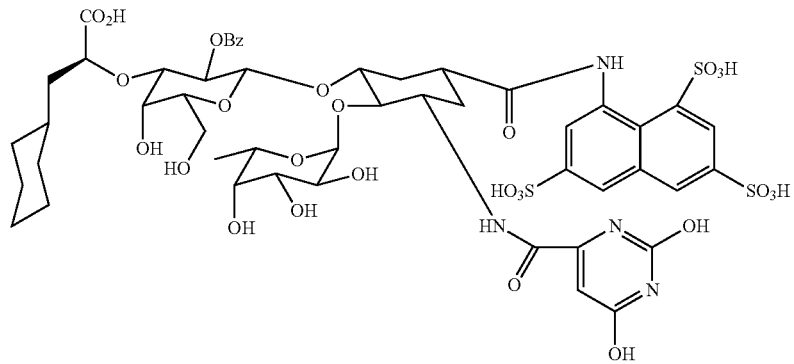

Where n is 1, a linker is present. A linker may be (or may include) a spacer group, such as —(CH$_2$)$_p$— or —O(CH$_2$)$_p$— where p is generally about 1-20 (including any whole integer range therein). Other examples of spacer groups include a carbonyl or carbonyl containing group such as an amide. An embodiment of such spacer groups is

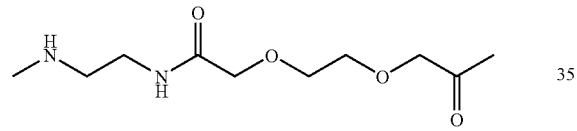

which produces:

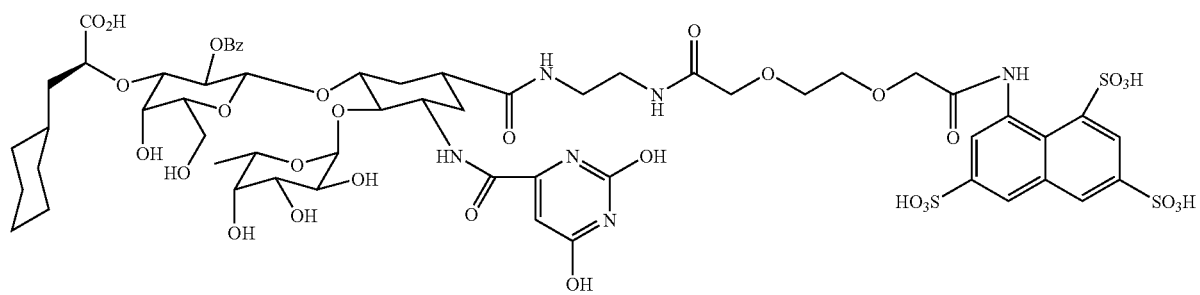

Embodiments of linkers include the following:

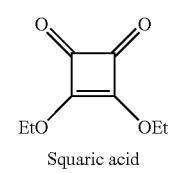
Squaric acid

Thiourea

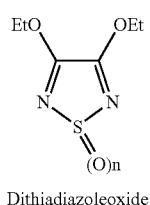
Dithiadiazoleoxide

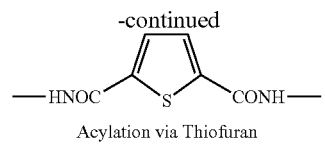
Acylation via Thiofuran

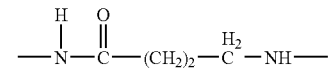
N-Pentenoylation and Reductive amination

-continued

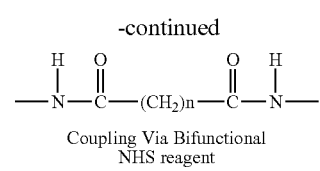
Coupling Via Bifunctional NHS reagent

Other linkers, e.g., polyethylene glycols (PEG) or —C(=O)—NH—(CH$_2$)$_p$—C(=O)—NH$_2$ where p is as defined above, will be familiar to those in the art or in possession of the present disclosure.

In another embodiment, the linker is

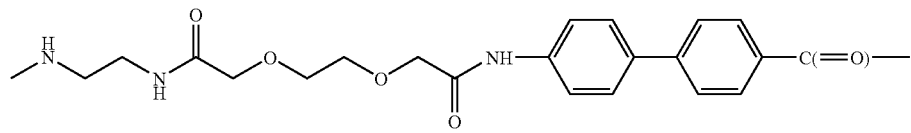

which produces:

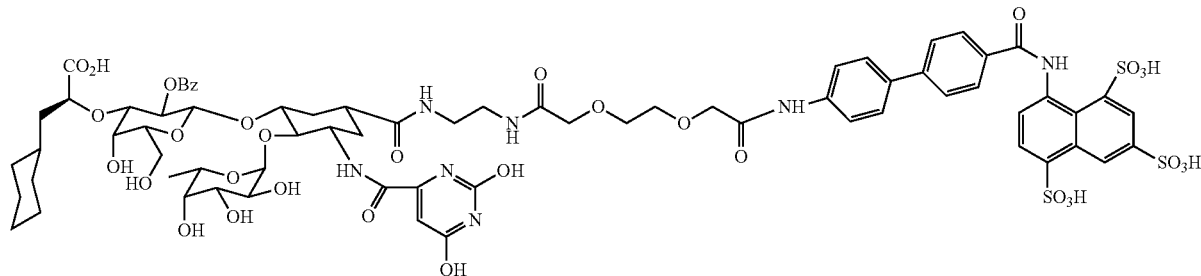

In another embodiment, the linker is

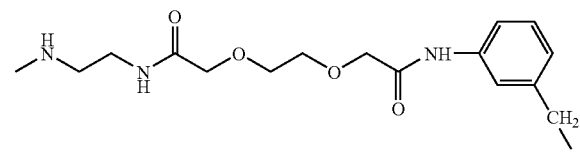 [SMILES: CCc1cccc(NC(=O)COCCOCC(=O)NCCNC)c1]

which produces:

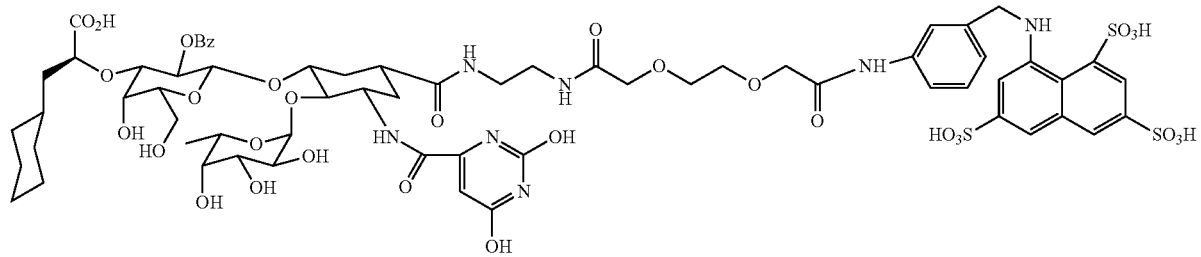

All compounds of the present invention or useful thereto (e.g., for pharmaceutical compositions or methods of treating), include physiologically acceptable salts thereof. Examples of such salts are Na, K, Li, Mg, Ca and Cl.

Compounds as described herein may be present within a pharmaceutical composition. A pharmaceutical composition comprises one or more compounds in combination with (i.e., not covalently bonded to) one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of compound release. The amount of compound contained within a sustained release formulation depends upon the site of implantation, the rate and expected duration of release and the nature of the condition to be treated or prevented.

The above described compounds including equivalents thereof are useful in methods of the present invention as it relates to cancers of the blood. Cancers of the blood include hematological malignancies. Examples of cancers of the blood include acute myelogenous leukemia (AML), acute lymphoblastic leukemia (ALL), chronic myelogenous leukemia (CML) and multiple myeloma (MM). In an embodiment, an individual who is in need of treatment for a cancer of the blood or a complication associated therewith is administered at least one (i.e., one or more) of the above described compounds in an amount effective for the treatment. As used herein, the term "treatment" (including variations such as "treating") includes prevention. For example, a complication associated with a cancer of the blood may not have presented itself in an individual with the disease, and a compound may be administered to prevent presentation of the complication in the individual. Complications associated with a cancer of the blood include, for example, shortened life expectancy, organ damage, periodic or chronic pain, migration of cancer cells out of blood circulation, and reduction in red blood cells, white blood cells or platelets. It is desirable to prevent cancer cells from leaving the primary site, or to prevent extravasation of cancer cells from the bloodstream and infiltration into other tissues. Cancer cells while in the bloodstream are typically susceptible to chemotherapy, but are more difficult to treat once they leave the bloodstream. For example, cancer cells (such as MM cells) can extravasate from the bloodstream and infiltrate into bone marrow matrix where they are inaccessible to chemotherapeutic agents circulating in the bloodstream. Consequences of the complication of migration of cancer cells out of blood circulation include relapse (failure to cure) and disseminated disease (metastasis) leading, for example, to organ damage or failure. AML is an example of a blood cancer with the complication of migration of cancer cells out of blood circulation resulting in disseminated disease.

The term "treatment," as set forth above, refers to any of a variety of positive effects from the treatment including, for example, eradicating a complication associated with the disease, relieving to some extent a complication, slowing or stopping progression of the disease, and prolonging the survival time of the recipient. The treatment may be used in conjunction with one or more other therapies for a cancer of the blood or complications associated therewith. Use of the treatment in conjunction with another therapy may be to provide two therapies each acting on their own to treat the cancer or a complication associated therewith, or may be to provide two therapies where one enhances the effectiveness of the other (e.g., increases the efficacy of the other or improves the outcome from the other) to treat the cancer or a complication associated therewith. For example, the treatment may be used to prevent or reduce the migration of cancer cells out of blood circulation. By acting to retain cancer cells in the bloodstream, the treatment enhances the effectiveness of another therapy which is used in conjunction and acts by providing a chemotherapeutic agent to the bloodstream.

The above described compounds including equivalents thereof are useful in methods of the present invention as it relates without regard to cancer type to reducing a myeloablative bone marrow toxicity of chemotherapy. This is applicable to cancers of the blood, but is not limited to cancers of the blood. Examples of toxicities include low white blood cell counts (e.g., low neutrophil counts), low red blood cell counts and low platelet counts. In an embodiment, an individual who is in need of reducing a myeloablative bone marrow toxicity of chemotherapy is administered at least one (i.e., one or more) of the above described compounds in an amount effective for the reducing. As used herein, the term "reducing" (including variations such as "reduction") includes partial and total reduction of at least one (i.e., one or more) myeloablative bone marrow toxicity of chemotherapy; and also includes partial and total prevention of at least one such toxicity (e.g., by administration of at least one of the above described compounds prior to, simultaneous with or shortly after, initiation of chemotherapy). For example, such a compound may not prevent neutropenia, but may promote a more rapid and sustained recovery of neutrophils after chemotherapy.

The above described compounds may be administered in a manner appropriate to the disease to be treated. Appropriate dosages and a suitable duration and frequency of administration may be determined by such factors as the condition of the patient, the type and severity of the patient's disease and the method of administration. In general, an appropriate dosage and treatment regimen provides the compound(s) in an amount sufficient to provide therapeutic and/or prophylactic benefit. Within particularly preferred embodiments of the invention, a compound may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated, which will be familiar to those of ordinary skill in the art.

At least one (i.e., one or more) of the above described compounds may be administered in combination with at least one (i.e., one or more) chemotherapeutic agents. The compound may function independent of the chemotherapeutic agent, or may function in coordination with the chemotherapeutic agent, e.g., by enhancing effectiveness of the agent or vice versa. In addition, the administration may be in conjunction with one or more other therapies for reducing toxicities of chemotherapy. For example, at least one (i.e., one or more) agent to counteract (at least in part) a side effect of chemotherapy may be administered. Drugs (chemical or biological) that promote recovery or enhancement of blood cells are examples of such agents. At least one compound described herein may be administered before, after or simultaneous with administration of at least one chemotherapeutic agent or at least one agent to reduce a side effect of chemotherapy. Where administration is simultaneous, the combination may be administered from a single container or two (or more) separate containers.

The following Examples are offered by way of illustration and not by way of limitation.

EXAMPLES

Example 1

Synthesis of BASA (FIG. 1)

Synthesis of compound 4: 3-nitro-benzyl iodide (1) (48.3 g) is added to an aqueous solution (pH 11) of commercially available, 8-aminonaphthalene-1,3,5-trisulfonic acid (2) (29.5 g) with stirring at room temperature (RT). The pH of the solution is adjusted to 1 and after evaporation of the solvent, the product 3 (6.4 g) is precipitated out from ethanol.

Platinum catalyzed hydrogenation of compound 3 affords compound 4 (the benzylamino sulfonic acid or "BASA" of FIG. 1) in 96% yield.

Example 2

Figure 2A:
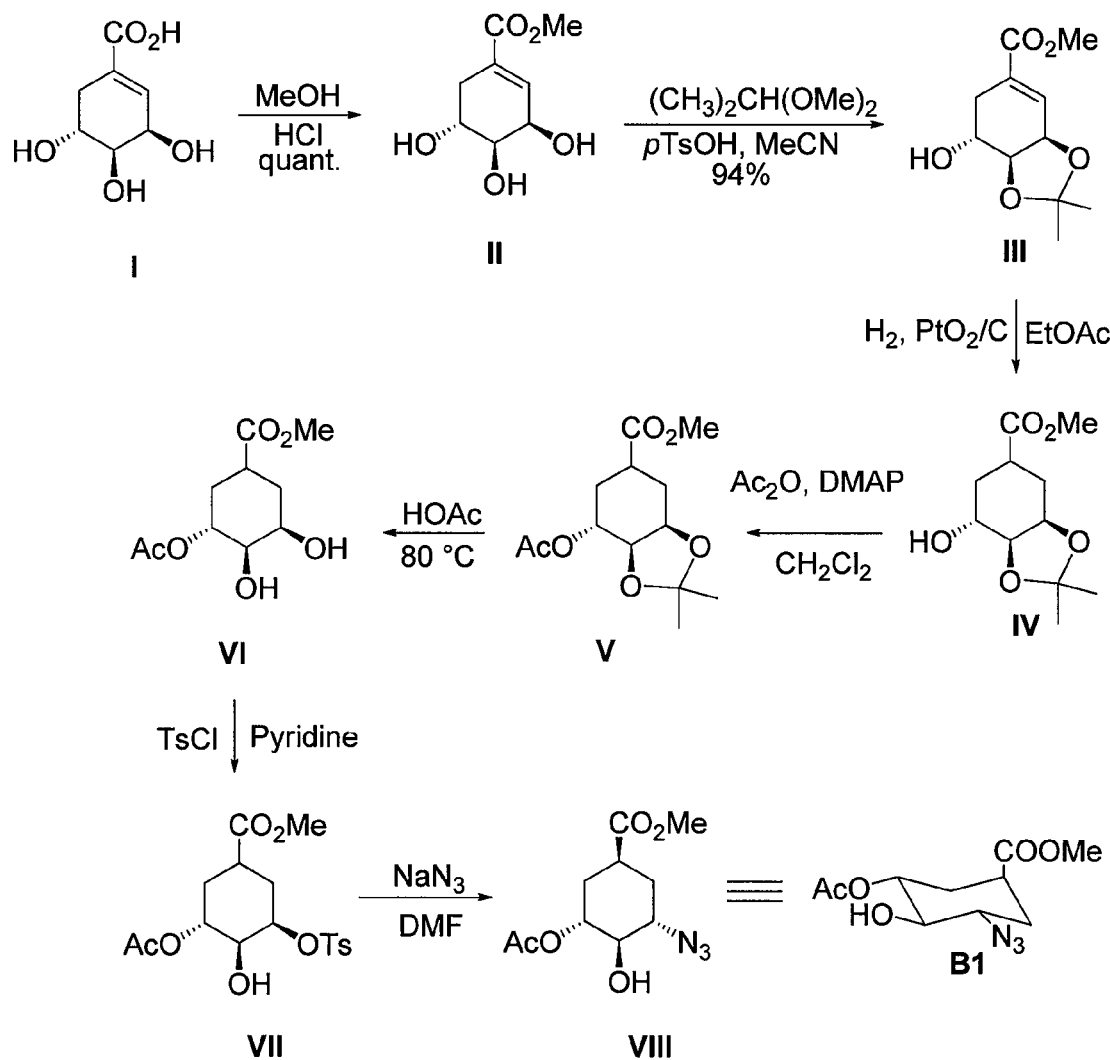
FIG. 2A-2C is a diagram illustrating the synthesis of a component of Compound #1.
Figure 2B:
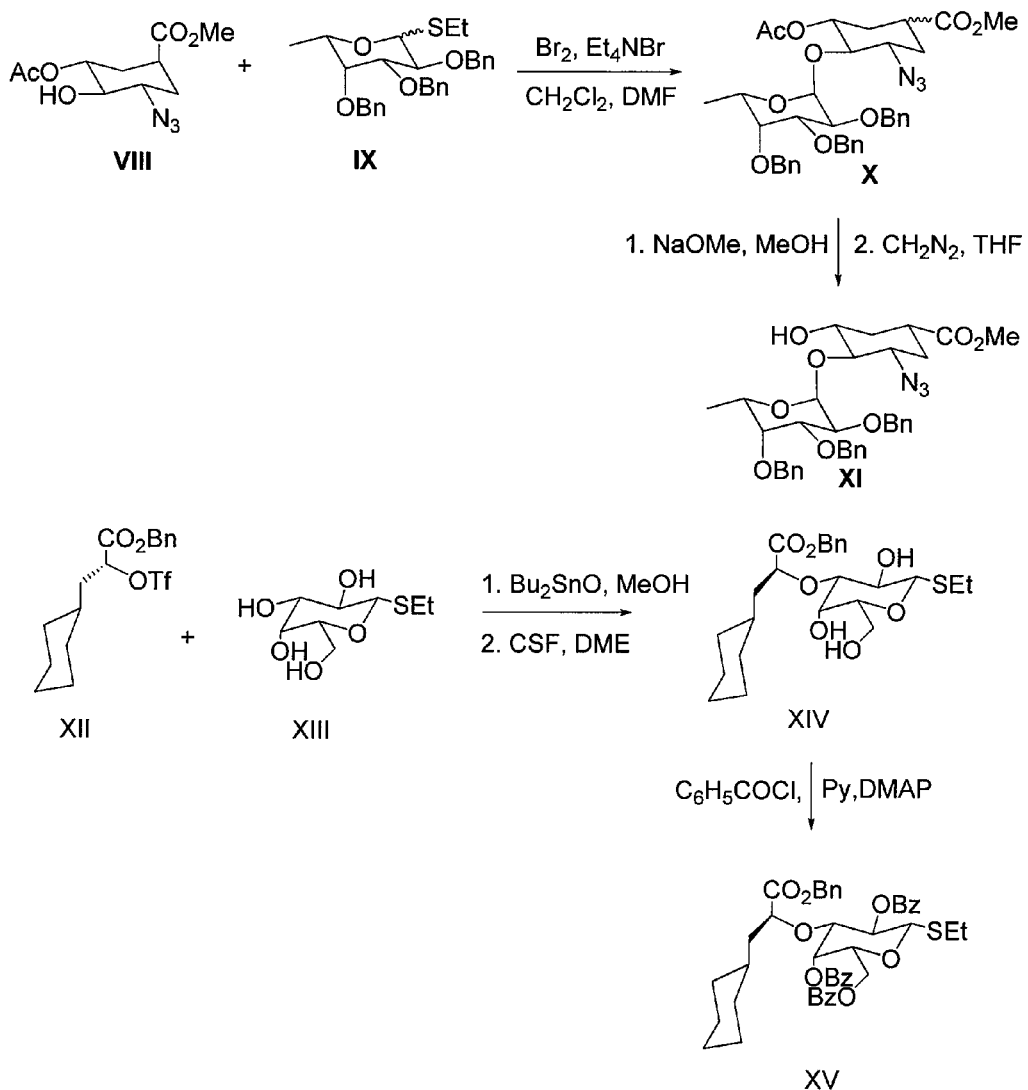
Figure 2C:
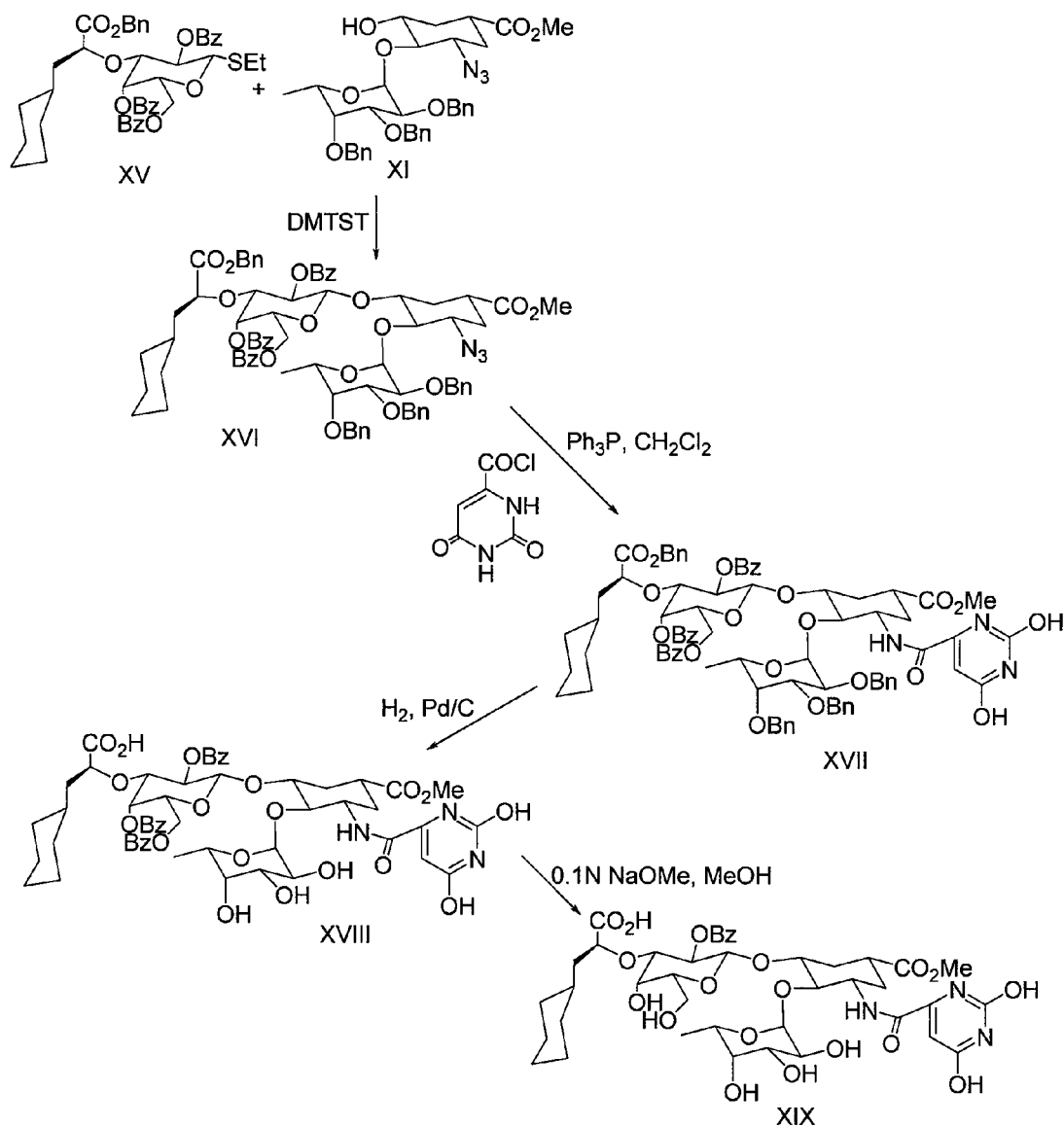

Synthesis of Glycomimetic (FIG. 2)

Synthesis of intermediate II: (−)-Shikimic acid (20 g) in MeOH (200 ml) and sulfuric acid (2 ml, 98%) are stirred at RT for 50 h. The reaction mixture is neutralized with 2N aqueous NaOH in the cold. After evaporation to dryness, the residue is purified by silica gel chromatography to afford II (19.2 g).

Synthesis of intermediate III: Methyl shikimate (II, 10 g), 2,2 dimethoxypropane (10 ml) and p-TsOH (0.8 g) are dissolved in acetonitrile (125 ml) and stirred at RT for 1 h. The reaction mixture is then neutralized with triethylamine (2 ml) and evaporated to dryness. The residue is chromatographed on silica gel to yield III (11 g).

Synthesis of intermediate IV: The shikimic acid derivative III (10 g) and $PtO_2/C$ (10%, 250 mg) in MeOH (40 ml) are hydrogenated at RT under vigorous stirring. After 16 h the reaction mixture is filtered over celite and evaporated to dryness. The residue is chromatographed on silica gel to yield IV.

Synthesis of intermediate V: To a solution of IV (8 g) in DCM (100 ml) at 0° C. are added pyridine (12 ml), acetic anhydride (7 ml) and a DMAP (25 mg). The reaction mixture is stirred at RT for 1 h, and diluted with EtOAc (250 ml). After washing with 0.5 M aqueous HCl (3×50 ml), saturated solution of $KHCO_3$ (3×50 ml) and brine (3×50 ml), the combined organic layers are dried ($Na_2SO_4$) and evaporated to dryness. The residue is purified by chromatography on silica gel to yield V (6.8 g).

Synthesis of intermediate VI: A solution of V (6.0 g) in acetic acid (30 ml, 80%) is stirred at 80° C. for 1 h. Solvent is evaporated off and the residue is purified by chromatography on silica gel (DCM/MeOH 14:1) to yield VI (3.6 g).

Synthesis of intermediate VII: A solution of VI (3 g) and p-TsCl (3.5 g) in pyridine (30 ml) is stirred at RT for 6 h. MeOH (5 ml) is added and the solvent is evaporated at reduced pressure, the residue dissolved in EtOAc (3×150 ml) and the organic layers are washed with 0.5 M aqueous HCl (0° C.), water (cold) and brine (cold). The combined organic layers are dried ($Na_2SO_4$), filtered on Celite and evaporated to dryness. The residue is purified by chromatography on silica gel (toluene/EtOAc 4:1) to yield VII (3.7 g).

Synthesis of compound VIII: A solution of VII (3 g) and $NaN_3$ (2.5 g) in DMF (20 ml) is stirred at 80° C. The reaction mixture is cooled to RT and diluted with EtOAc (200 ml) and water (50 ml). The organic layer is additionally washed twice with water (2×50 ml) and once with brine (50 ml). All aqueous layers are extracted twice with EtOAc (2×50 ml). The combined organic layers are dried with $Na_2SO_4$, filtered and the solvent is evaporated off. The residue is purified by chromatography on silica gel (petroleum ether/EtOAc 5:2) to give VIII (2.2 g).

Synthesis of compound X: To a solution of ethyl 2,3,4-tri-O-benzyl-α-L-fucothiopyanoside IX (1.5 g) in DCM (3 ml), bromine (150 µl) is added at 0° C. under argon. After 5 min the cooling bath is removed and the reaction mixture is stirred for an additional 25 min at RT. Cyclohexene (200 µl) is added and the reaction mixture is added to a solution of VIII (400 mg), $(Et)_4NBr$ (750 mg) and powdered 4 Å molecular sieves in DCM (10 ml) and DMF (5 ml). After 16 h, triethylamine (1.5 ml) is added and stirred for an additional 10 min, diluted with EtOAc (50 ml) and washed with sat. aqueous $NaHCO_3$, water and brine. The aqueous layers are extracted twice with EtOAc (2×50 ml). The combined organic layers are dried ($Na_2SO_4$), filtered and evaporated to dryness. The residue is purified by chromatography on silica gel (toluene/EtOAc 9:1) to yield X (700 mg).

Synthesis of compound XI: To a solution of X (1.5 g) in MeOH (20 ml) is added freshly prepared NaOMe (80 mg) and the reaction mixture is stirred in a pressure tube at 80° C. for 20 h. The reaction mixture is cooled to RT and neutralized with acetic acid. Solvent is evaporated to dryness and the residue is dissolved in ether. Freshly prepared diazomethane is added and the excess diazomethane is neutralized with acetic acid. Solvent is evaporated off to give XI (1.25 g).

Synthesis of building block XV: This synthesis is done exactly in same way as described previously (*Helvetica Chimica Acta* 83:2893-2907 (2000)).

Synthesis of compound XVI: A mixture of XI (1.6 g), XV (3 g) and activated powdered molecular sieves 4 Å (1 g) in DCM (17 ml) is stirred at RT under argon for 2 h. Then DMTST (2 g) is added in 4 equal portions over a period of 1.5 h. After 24 h the reaction mixture is filtered over Celite and the filtrate is diluted with DCM (100 ml). The organic layer is washed with sat. aqueous $NaHCO_3$ and brine and the aqueous layers are extracted twice with DCM. The combined organic layers are dried ($Na_2SO_4$), filtered and evaporated to dryness. The residue is purified by chromatography on silica gel (toluene/EtOAc 8:1) to yield XVI (1.5 g).

Synthesis of compound XVII: To a solution of XVI (500 mg) and orotic acid chloride (500 mg) in dichloromethane (10 ml) is added a solution of triphenylphosphine (500 mg in 5 ml dichloromethane) dropwise during 10 min. The reaction mixture is stirred at RT for 25 h and the solvent is evaporated off. The residue is purified (chromatography on silica gel DCM/MeOH 19:1) to give XVII (250 mg).

Synthesis of compound XVIII: To a solution of XVII (200 mg) in dioxane-water (5:1, 12 ml) is added 10% Pd—C (100 mg) and the reaction mixture is stirred vigorously under hydrogen (55 psi) for 24 h. Catalyst is filtered through a bed of celite and the solvent is evaporated off. Residue is purified by silica gel chromatography to give compound XVIII (150 mg).

Synthesis of XIX: To a solution of compound XVIII (145 mg) in MeOH (5 ml) is added a solution of NaOMe in MeOH (25%, 0.025 ml) and the reaction mixture is stirred at RT for 4 h, neutralized with acetic acid and the solvent is evaporated off. Residue is dissolved in water and passed through a bed of Dowex 50wX-8 (Na-form) resin. Water wash is evaporated off to afford compound XIX (100 mg).

Synthesis of EDA-XIX: XIX (80 mg) is heated at 70° C. with ethylenediamine (EDA) (1 ml) with stirring for 5 h. Solvent is evaporated off and the purified by sephadex G-25 column to give EDA-XIX (82 mg).

Example 3

Figure 3:
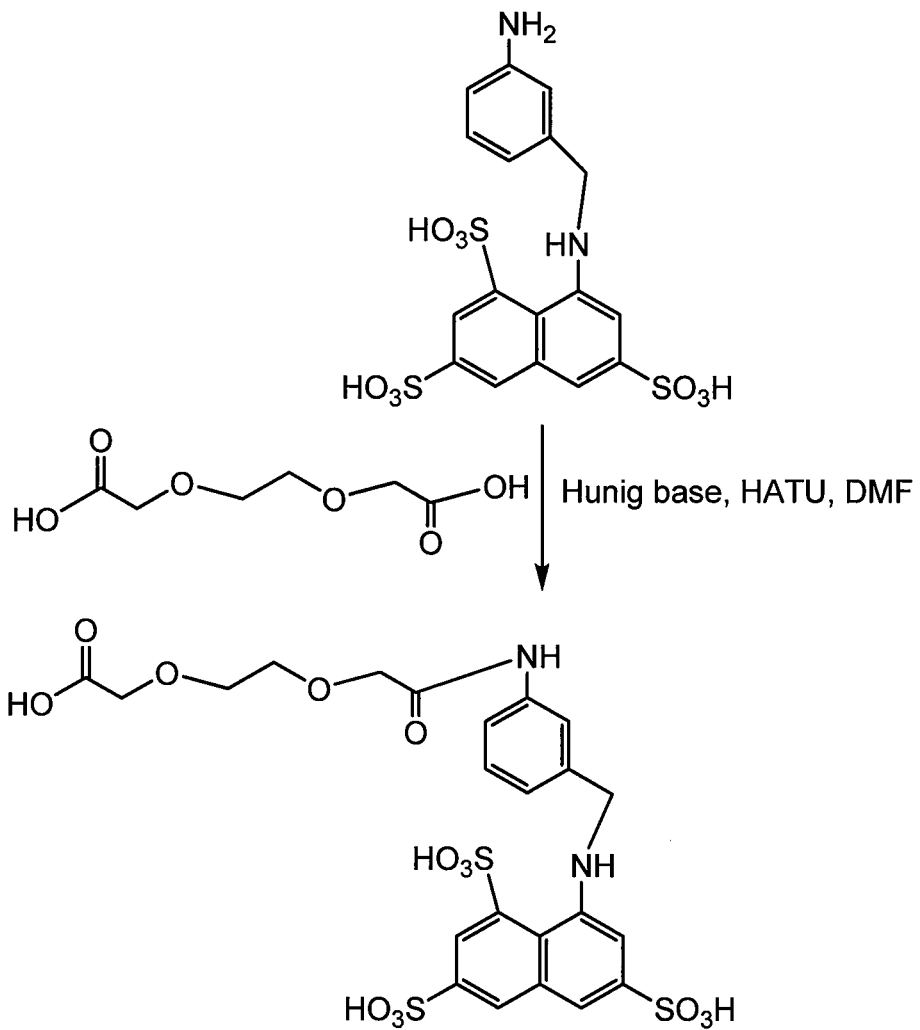
FIG. 3 is a diagram illustrating the modification of the component of FIG. 1.

Synthesis of PEGylated BASA (FIG. 3)

To a solution of 3,6-dioxaoctanedioic acid (PEG, 200 mg, available commercially) in DMF (1 ml) is added Hunig base (0.4 ml), and then HATU (0.35 g) is added after 5 min. The solution is stirred at RT for 10 min. and then a solution of the BASA of Example 2 (50 mg) in DMF (0.1 ml) is added. The reaction mixture is stirred for 4 h at RT and the solvent is evaporated off. The residue is purified by hplc (reverse-phase C18 column) to give XX (40 mg).

Example 4

Figure 4:
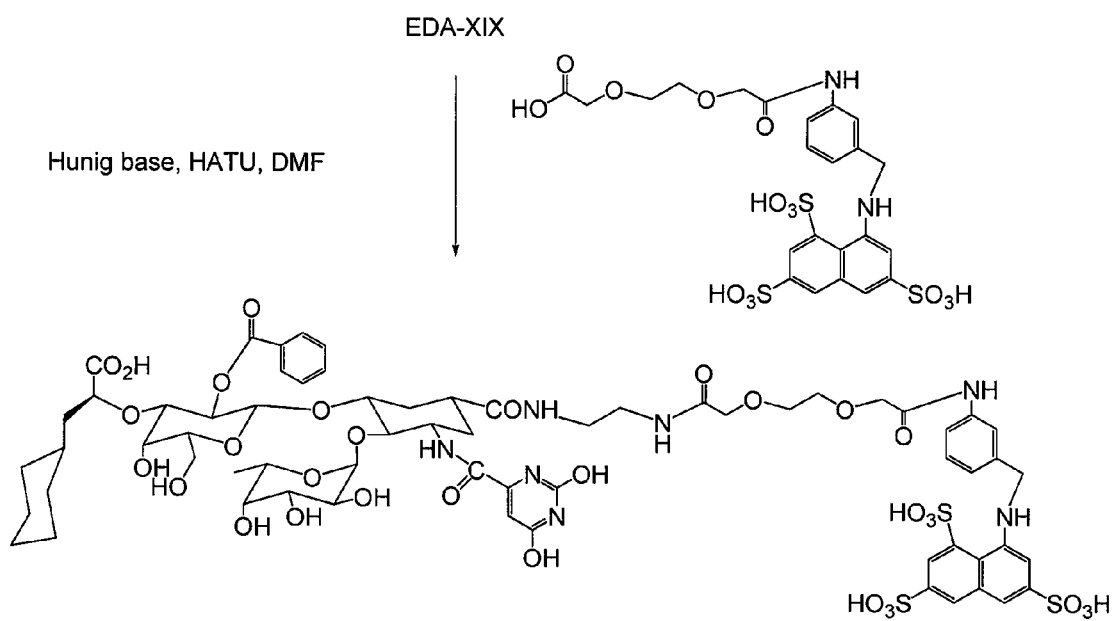
FIG. 4 is a diagram illustrating the reaction of the components of FIGS. 2 and 3 to form Compound #1. Compound XIX of FIG. 2 is reacted with ethylenediamine (EDA) to form EDA-XIX.

Synthesis of Glycomimetic-BASA Compound #1 (FIG. 4)

To a solution of XX from Example 3 (0.015 g) in DMF (0.1 ml) is added Hunig base (0.015 ml) and then HATU (0.007 g). The reaction mixture is stirred for 10 min at RT. A solution of EDA-XIX from Example 2 (0.010 g in DMF ml) is added and the reaction mixture is stirred at RT for 8 h. Solvent is evaporated off and the residue is purified by sephadex G-25 chromatography to give the Glycomimetic-BASA #1 of FIG. 4 (0.008 g).

Example 5

Figure 5:
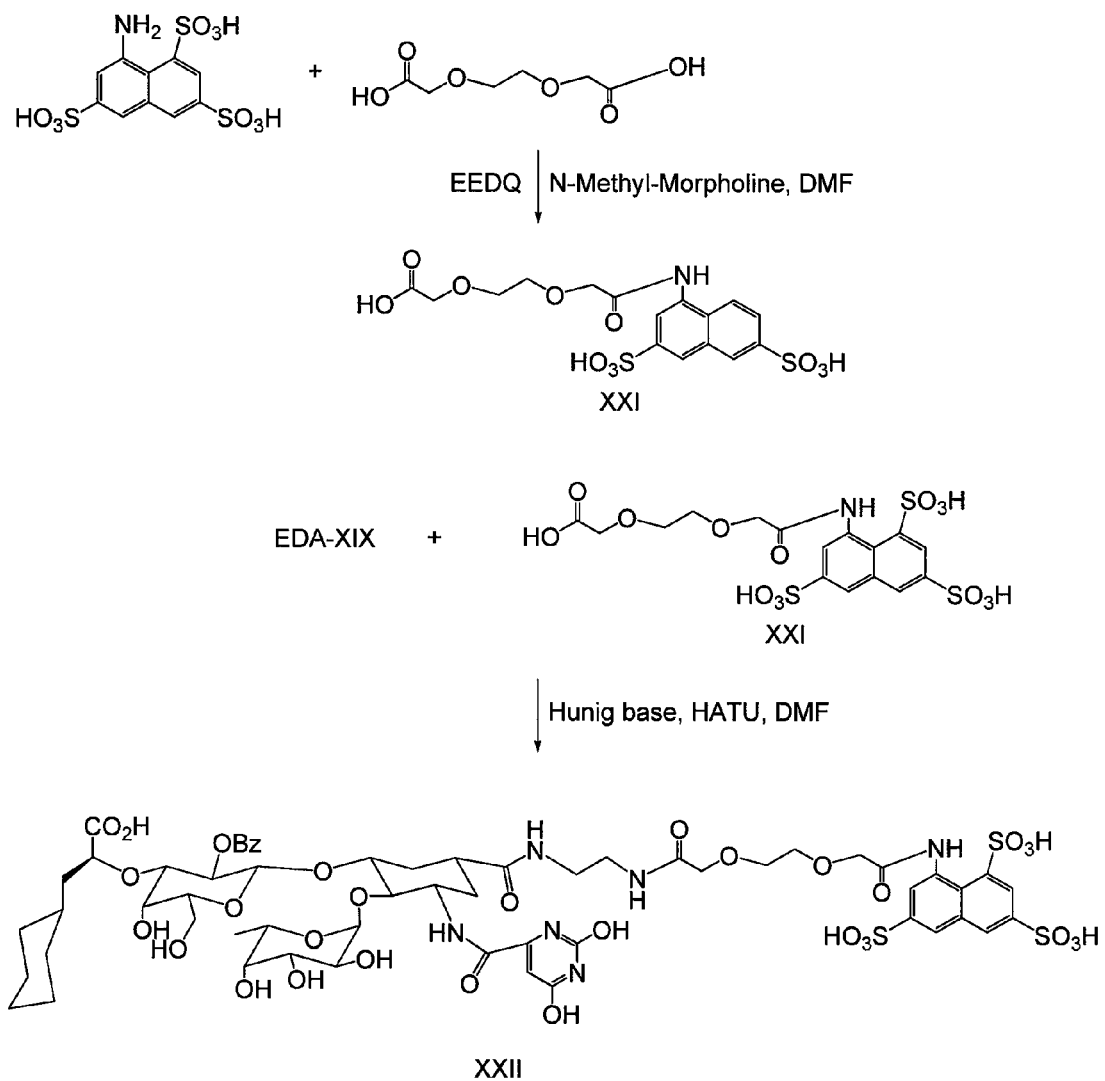
FIG. 5 is a diagram illustrating the synthesis of Compound #2. Compound XIX of FIG. 2 is reacted with ethylenediamine (EDA) to form EDA-XIX.

Synthesis of Glycomimetic-BASA Compound #2 (FIG. 5)

Synthesis of compound XXI: To a solution of 3,6-dioxaoctanedioic acid (PEG, 200 mg, available commercially) in DMF (1 ml) is added Hunig base (0.4 ml) and then HATU (0.35 g) is added after 5 min. The solution is stirred at RT for 10 min and then a solution of 8-aminonaphthalene-1,3,6-trisulfonic acid (50 mg, available commercially) in DMF is added. The reaction mixture is stirred for 4 h at RT and the solvent is evaporated off. The residue is purified by hplc (reverse-phase C18 column) to give XXI (25 mg).

Synthesis of compound XXII: This synthesis is performed in the same way as described in example 4 except using EDA-XIX from example 2 and XXI to give compound XXII (4 mg).

Example 6

Figure 6:
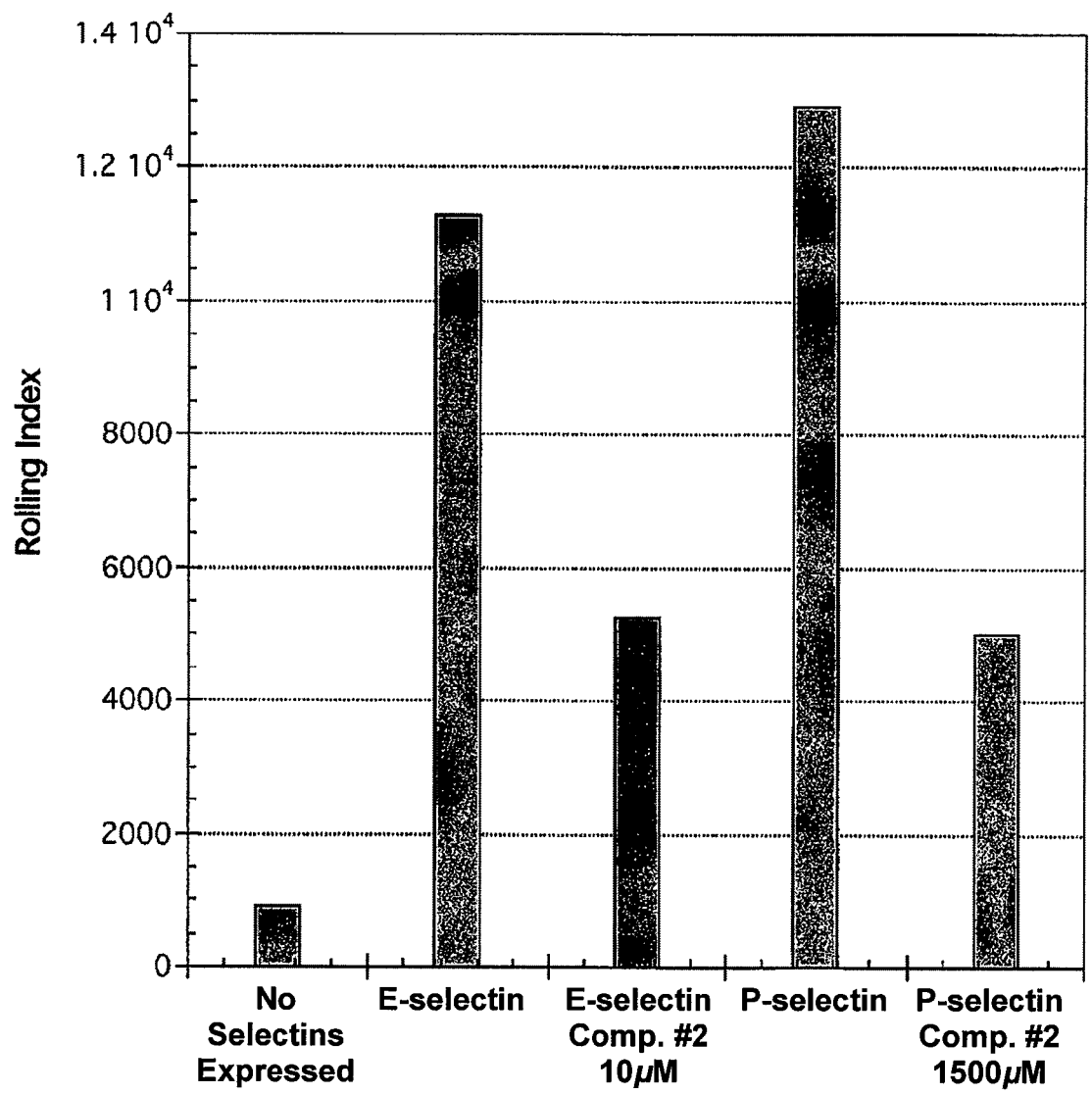
FIG. 6 shows that Compound #2 inhibits both E-selectin and P-selectin AML rolling on human endothelial cells.

Effects of Compound #2 on E-Selectin and P-Selectin AML Rolling on Human Endotheleial Cells Interaction of AML cells with the vascular endothelium is an early step in the extravasation of the cancer cells out of the circulation. Experiments are conducted within the present invention to demonstrate that a human AML cell line (MV-4-11 derived from biphenotypic B myelomonocyte leukemia) interacts with, and rolls on, human umbilical vein endothelial cells (HUVECs) in vitro stimulated to express either E-selectin or P-selectin. As shown in FIG. 6, glycomimetic compound #2 (Example 5; FIG. 5) inhibits the rolling of the AML cells on the stimulated HUVECs.

Example 7

Figure 7:
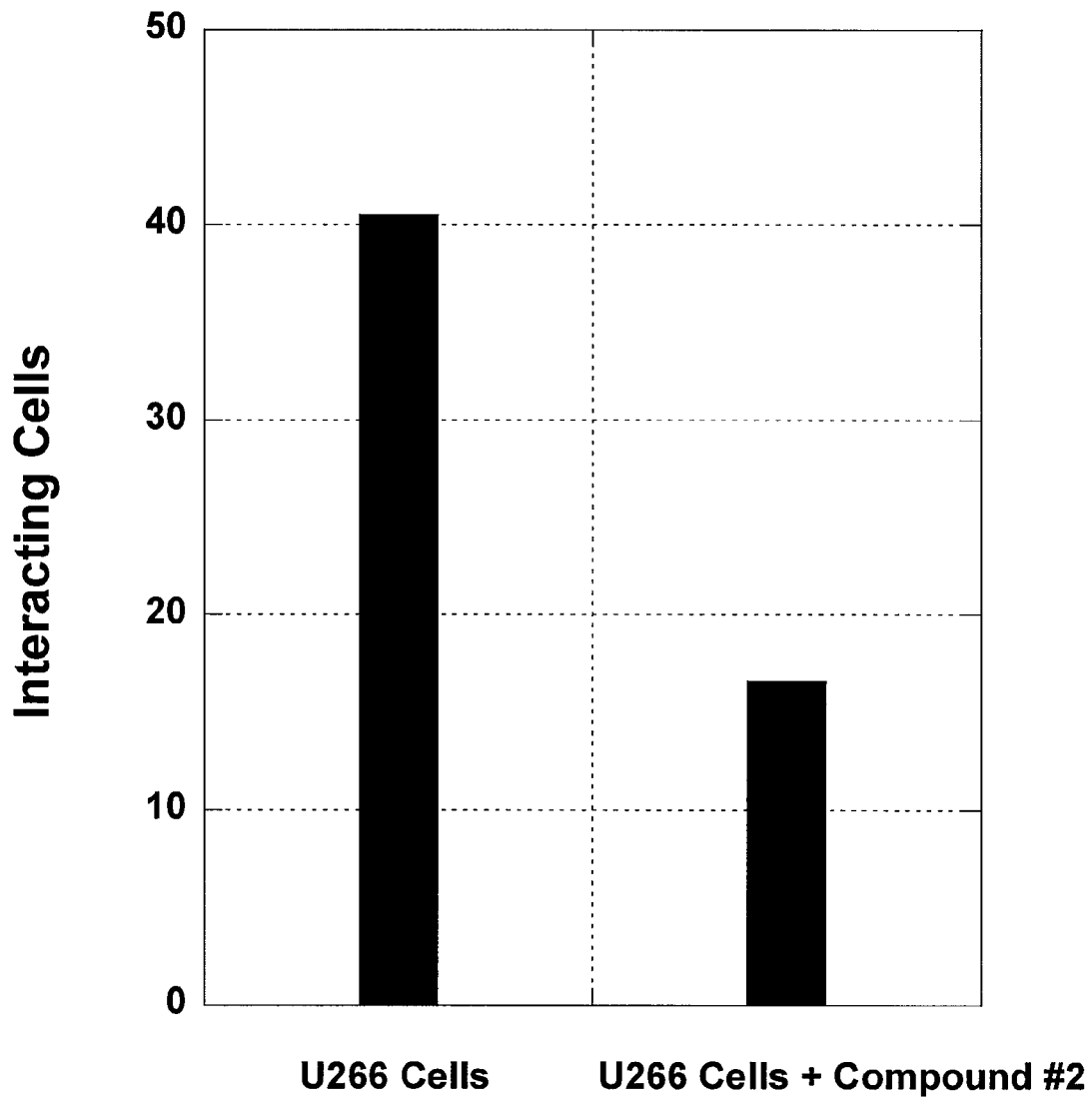
FIG. 7 shows the effect of Compound #2 (at 1.5 mM) on U266 myeloma cell adhesion to endothelial cells expressing P-selectin under flow conditions.

Effects of Compound #2 on P-Selectin-Mediated Rolling and Adhesion of Multiple Myeloma Cell Line U266 on Human Endothelial Cells Under Flow Conditions Interaction of multiple myeloma cells with the vascular endothelium is an early step in the extravasation of cancer cells out of the bloodstream. Experiments are conducted within the present invention to demonstrate that a human multiple myeloma cell line (U266) interacts with (rolls and adheres) a monolayer of human umbilical vein endothelial cells (HUVECs) stimulated to express P-selectin. Interactions under the shear forces of normal blood flow (1 dyne/cm2) are quantified by digital image analysis. As shown in FIG. 7, Compound #2 (Example 5; FIG. 5) inhibits over 50% of cancer cell interactions with the endothelial monolayer expressing P-selectin at 1.5 mM.

Example 8

Figure 8:
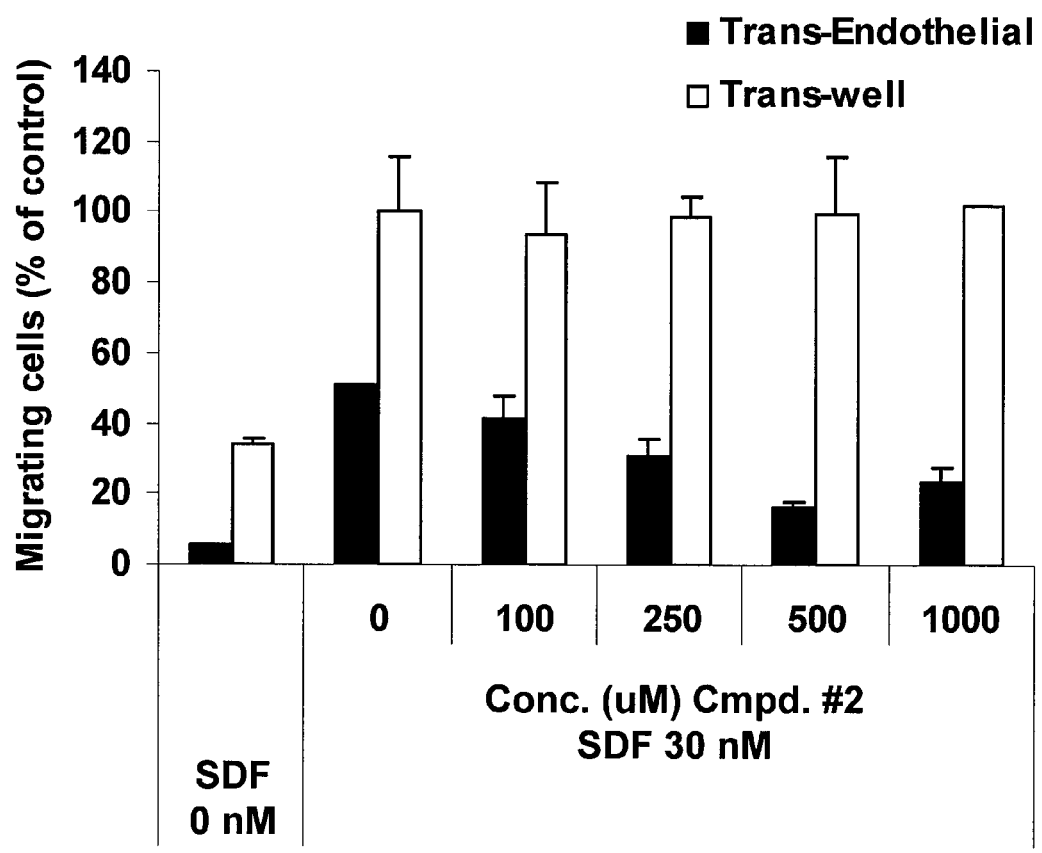
FIG. 8 shows the effect of Compound #2 (at various concentrations) on SDF-1 induced transendothelial migration of multiple myeloma (MM) cells.

Effects of Compound #2 on the SDF-1 Trans-Membrane and Trans-Endothelial Migration of Multiple Myeloma Cells In order to home to the bone marrow or disseminate to other tissues from the bloodstream, multiple myeloma cells must first traverse through the vascular endothelium. An in vitro model of this process is established with transwell plates in which each well is divided into 2 chambers by a bisecting membrane. The chemokine, stromal cell derived factor-1 (SDF-1) (30 nM) is placed in the lower chamber and the percentage of multiple myeloma cells that migrate from the upper chamber to the lower chamber is quantified. The experiment is conducted with membrane alone (open bars) or with the membrane covered with a monolayer of endothelial cells (HUVECs). As can be seen in FIG. 8, Compound #2 (Example 5; FIG. 5) inhibits migration specifically through the endothelial monolayer, suggesting inhibition is based on target molecules (i.e., selectins) on the endothelial cells.

Example 9

Figure 9:
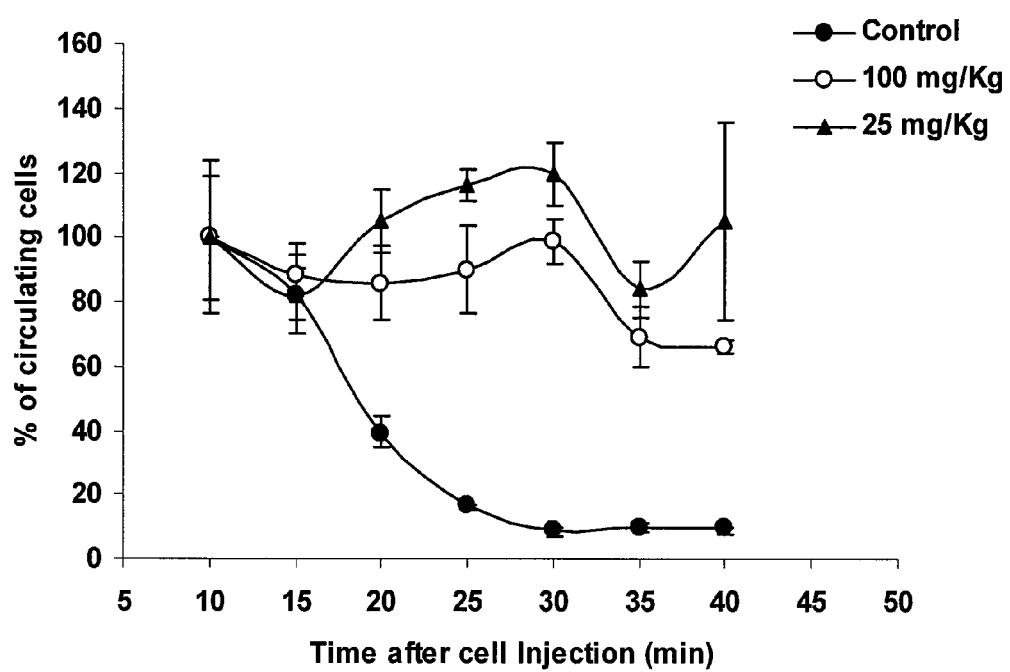
FIG. 9 shows the effect of Compound #2 (at 25 mg/kg or 100 mg/kg) on the extravasation of multiple myeloma cells from the bloodstream in vivo.

Effects of Compound #2 on the Extravasation of Multiple Myeloma Cells from the Bloodstream In Vivo Human Multiple Myeloma (MM) cells injected into mice extravasate from the bloodstream and home to the bone marrow and other organs within minutes. By fluorescently labeling MM cells, this process can be monitored in vivo by intravital microscopy using confocal microscopic techniques. As shown in FIG. 9, within 30 minutes almost all of the MM cells have left the peripheral bloodstream. Co-injection of cells with Compound #2 at two different doses (100 mg/kg and 25 mg/kg) dramatically inhibits this extravasation of circulating MM cells in vivo.

Example 10

Inhibition of Bone Marrow Engraftment of AML Cells

NOD/SCID/IL2 receptor γ chain$^{null}$ mice ("irradiated mice") are obtained (Ishikawa et al., Nat. Biotech. 25:1315-1321, 2007; Christianson et al., J. Immunol. 158:3578-3586, 1997; Cao et al., Immunity 2:223-238, 1995). The AML cell line used in Example 6 is administered intravenously into irradiated mice (control group). The AML cell line engrafts into the bone marrow of the irradiated mice. Other irradiated mice (experimental group) are intravenously administered glycomimetic compound #2, followed after a time interval by intravenous administration of the AML cell line. In other irradiated mice (a different experimental group), the order of administration is reversed with the AML cell line administered intravenously first, followed after a time interval by intravenous administration of glycomimetic compound #2. Bone marrow engraftment by the AML cell line is assessed by histological and flow cytometry analysis.

Example 11

Effects of Compound #2 on Chemotherapy-Induced Neutropenia

Many chemotherapeutic drugs kill cancer cells by targeting the enhanced cell proliferation associated with malignancy. Side effects of these drugs include the increased toxicity of normal cells undergoing cell division such as the hematopoietic stem cells (HSC) that are required for the generation of new blood. In particular, one of the clinically relevant side effects of standard chemotherapy drugs in patients is the dramatic reduction of neutrophils that are required to fight infections. Low neutrophil counts contribute to the immune compromised condition of cancer patients that leaves them vulnerable to potentially life threatening infections. A rapid recovery of the immune system after a course of chemotherapy is a highly desirable goal among this population.

To determine whether inhibition of selectins has a beneficial effect on protection and recovery of neutrophils from treatment with anti-proliferative drugs, mice are treated with Compound #2 pre- and post-administration of either 5-fluorouracil (5-FU) or cyclophosphamide. At varying time points after treatment, blood samples are taken from the mice and analyzed for different cell types including neutrophils.

Figure 10:
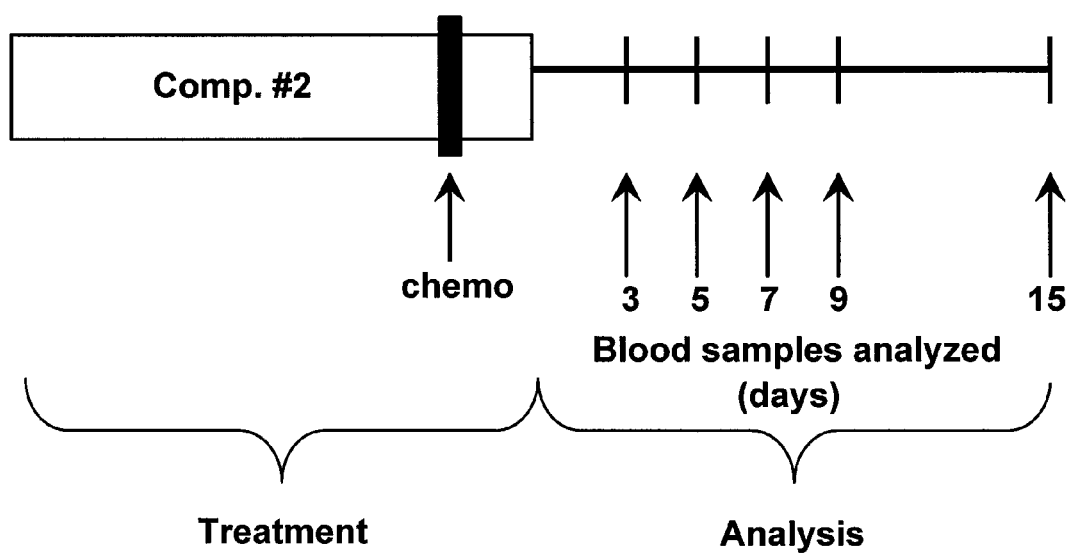
FIG. 10 is a schematic diagram of the protocol for studying the effects of Compound #2 on chemotherapy-induced neutropenia.

As diagrammed in FIG. 10, mice are treated with Compound #2 for 14 days by intraperitoneal injections (50 mg/kg) twice a day. On day 12 within this treatment period, a cohort of mice receives an injection of a chemotherapeutic drug; either 5-fluorouracil (150 mg/kg i.p.) or cyclophosphamide (300 mg/kg i.p.). On the third day after treatment with Compound #2, blood is obtained by cardiac puncture from one cohort of mice to determine a complete blood count (CBC). Other cohorts of mice are bled and analyzed (CBC) on days 5, 7, 9 and 15 after Compound #2 treatment.

Figure 11:
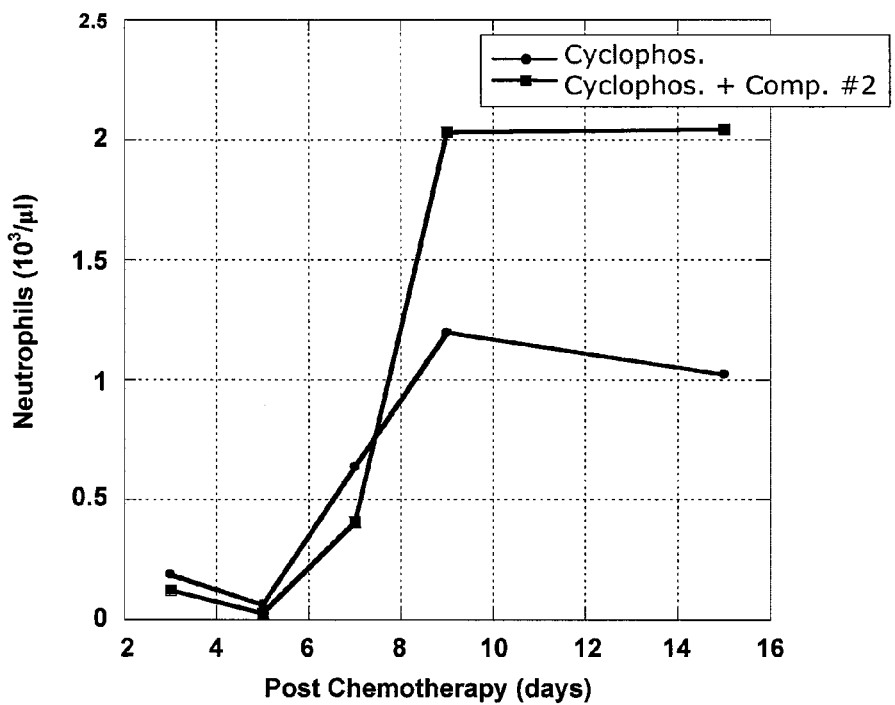
FIG. 11 shows the effect of Compound #2 on the recovery of neutrophils in mice treated with cyclophosphamide.
Figure 12:
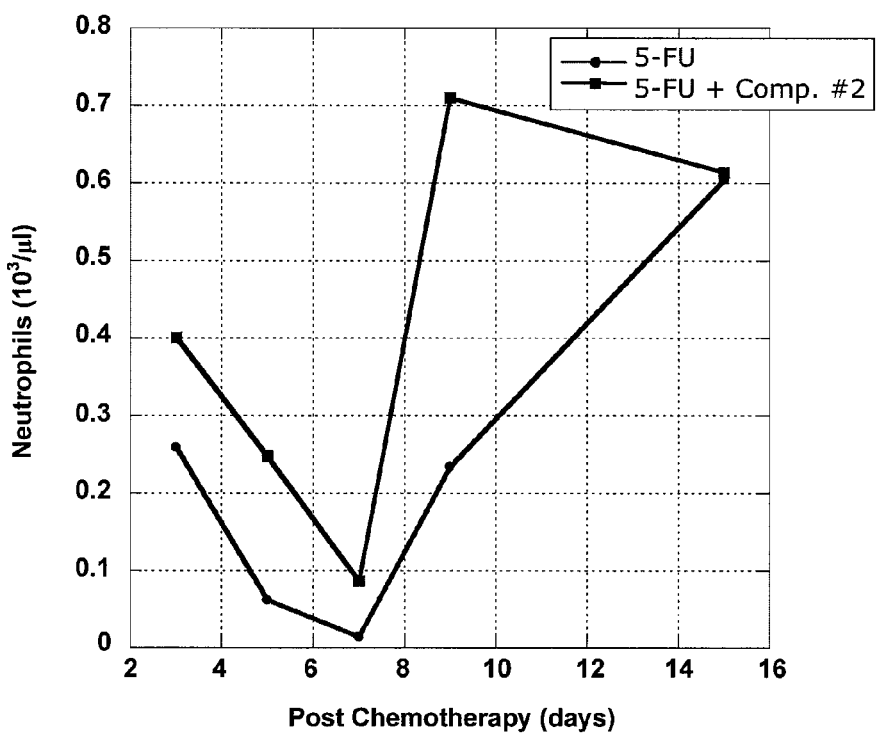
FIG. 12 shows the effect of Compound #2 on the recovery of neutrophils in mice treated with 5-FU.

The chemotherapeutic drugs, 5-FU and cyclophosphamide have the most pronounced effects on the numbers of neutrophils in the blood. Both 5-FU and cyclophosphamide cause severe neutropenia in mice that lasts for at least one week. A few days after treatment by these drugs, the numbers of neutrophils in the blood declines to dangerously low levels as shown in FIGS. 11 and 12. Pre-treatment of mice with Compound #2 markedly improves recovery of neutrophil counts after administration of either cyclophosphamide (FIG. 11) or 5-FU (FIG. 12). Compound #2 treatment by itself also promotes increased levels of neutrophils in the blood (data not shown). While Compound #2 does not prevent neutropenia in mice treated with either 5-FU or cyclophosphamide, it does promote a more rapid and sustained recovery of neutrophils after drug treatment and therefore may be useful in combination with standard chemotherapy of cancer patients.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:
1. A method of inhibiting metastasis of a cancer of the blood in an individual, comprising administering to the individual a compound in an amount effective for inhibiting metastasis, the compound having the formula:

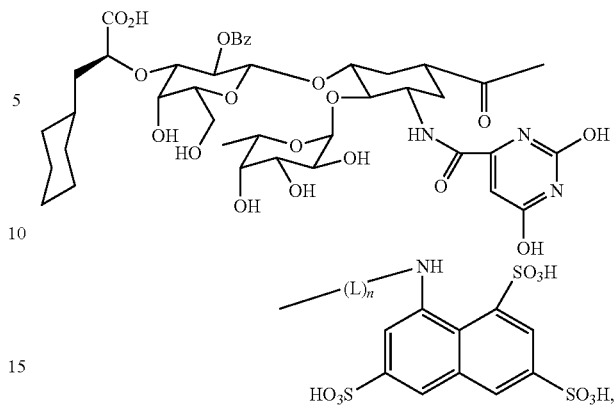

or a physiologically acceptable salt thereof, wherein
L=linker group; and
n=0-1.

2. The method according to claim 1, wherein in the compound n=0.

3. The method according to claim 1, wherein in the compound n=1 and L is

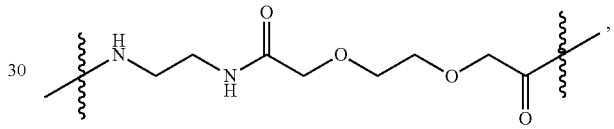

where the terminal N of L is attached to terminal C of C(=O) of the compound.

4. The method according to claim 1, wherein in the compound n=1 and L is

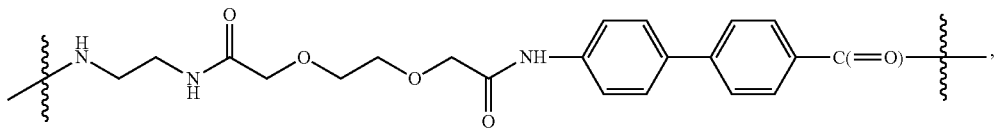

where the terminal N of L is attached to terminal C of C(=O) of the compound.

5. The method according to claim 1, wherein in the compound n=1 and L is

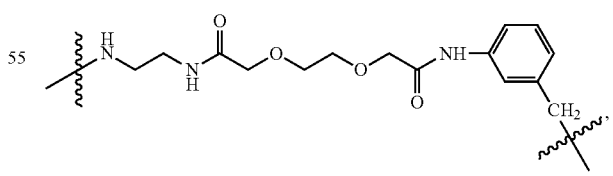

where the terminal N of L is attached to terminal C of C(=O) of the compound.

6. The method according to claim 1, wherein the cancer is acute myelogenous leukemia (AML).

7. The method according to any one of claims 1-6, wherein the compound is in combination with a pharmaceutically acceptable carrier or diluent.

\* \* \* \* \*